(12) United States Patent
Lee et al.

(10) Patent No.: US 10,172,535 B2
(45) Date of Patent: Jan. 8, 2019

(54) WEARABLE DEVICE AND METHOD FOR PROVIDING FEEDBACK INFORMATION THROUGH VEIN AUTHENTICATION

(71) Applicant: SK PLANET CO., LTD., Gyeonggi-do (KR)

(72) Inventors: Daewoo Lee, Gyeonggi-do (KR); Seulmaro Jeon, Gyeonggi-do (KR)

(73) Assignee: SK PLANET CO., LTD., Seongnam-si, Gyeonggi-Do (KR)

(*) Notice: Subject to any disclaimer, the term of this patent is extended or adjusted under 35 U.S.C. 154(b) by 140 days.

(21) Appl. No.: 15/299,092

(22) Filed: Oct. 20, 2016

(65) Prior Publication Data

US 2017/0119276 A1 May 4, 2017

(30) Foreign Application Priority Data

Oct. 28, 2015 (KR) .................. 10-2015-0150322
Oct. 29, 2015 (KR) .................. 10-2015-0150977
Oct. 30, 2015 (KR) .................. 10-2015-0152109

(51) Int. Cl.
| | | |
|---|---|---|
| *G06F 19/00* | (2018.01) | |
| *A61B 5/053* | (2006.01) | |
| *A61B 5/1171* | (2016.01) | |
| *G06F 21/32* | (2013.01) | |
| *A61B 5/00* | (2006.01) | |
| *A61B 5/11* | (2006.01) | |
| *G06K 9/00* | (2006.01) | |
| *G16H 40/63* | (2018.01) | |

(52) U.S. Cl.
CPC ............ *A61B 5/0537* (2013.01); *A61B 5/112* (2013.01); *A61B 5/1171* (2016.02); *G06F 19/3418* (2013.01); *G06F 21/32* (2013.01); *A61B 5/0022* (2013.01); *A61B 5/1112* (2013.01); *A61B 5/1118* (2013.01); *A61B 5/1123* (2013.01); *G06K 9/00348* (2013.01); *G06K 2009/00932* (2013.01); *G16H 40/63* (2018.01)

(58) Field of Classification Search
CPC .......................... G06F 19/3418; G06F 21/32
USPC ......................................................... 382/128
See application file for complete search history.

(56) References Cited

U.S. PATENT DOCUMENTS

| | | | | |
|---|---|---|---|---|
| 2015/0040203 A1* | 2/2015 | Qian | ....................... | G06F 21/32 726/7 |
| 2015/0063661 A1* | 3/2015 | Lee | ......................... | G06F 3/011 382/124 |

(Continued)

FOREIGN PATENT DOCUMENTS

| | | |
|---|---|---|
| KR | 10-1062011 B1 | 9/2011 |
| KR | 2015-0069086 A | 6/2015 |

*Primary Examiner* — Raj Chakraborty
(74) *Attorney, Agent, or Firm* — Fenwick & West LLP

(57) ABSTRACT

Disclosed herein are a wearable device and method for providing feedback information through vein authentication or the measurement of a body composition. In an aspect, the wearable device may include a measurement module configured to measure the pattern of veins of a user, a communication module configured to send unique bio information about the user measured by the measurement module to a management server along with authentication information and to receive feedback information for the transmitted information from the management server, and a memory module configured to store the pattern of the veins of the user.

7 Claims, 26 Drawing Sheets

(56) References Cited

U.S. PATENT DOCUMENTS

2016/0198977 A1* 7/2016 Eom .................... A61B 5/0537
                                                      600/384
2016/0310341 A1* 10/2016 Yu ............................ G09B 5/02

* cited by examiner

WEARABLE DEVICE AND METHOD FOR PROVIDING FEEDBACK INFORMATION THROUGH VEIN AUTHENTICATION

CROSS REFERENCE TO RELATED APPLICATION

The present application claims the benefit of Korean Patent Application No. 10-2015-0152109 filed in the Korean Intellectual Property Office on Oct. 30, 2015, Korean Patent Application No. 10-2015-0150322 filed in the Korean Intellectual Property Office on Oct. 28, 2015 and Korean Patent Application No. 10-2015-0150977 filed in the Korean Intellectual Property Office on Oct. 29, 2015, the entire contents of which are incorporated herein by reference.

BACKGROUND OF THE INVENTION

1. Technical Field

The present invention relates to a wearable device and method for providing feedback information through vein authentication or the measurement of a body composition and, more particularly, to a wearable device including a measurement module configured to identify a person through the authentication of veins of a user and to measure a body composition of the user, a control module configured to calculate the physical condition of the user based on the measured state, and a communication module configured to send information about the measured body composition and vein to a management server and to receive feedback information for the transmitted information from the management server.

2. Description of the Related Art the human body, and includes various types of devices, such as glasses, a watch, a bracelet, shoes, a ring, a belt, a band, a necklace, a headset, and clothing, depending on a part on which the device is worn. Today, such a wearable device is coming into wide use. From among the wearable devices, the wearable glasses, the wearable watch, and the wearable band which are very closely related to the human life and can be easily worn form the most product group.

The wearable device is also called a smart device. The reason for this is that the wearable device needs to be initially driven by user input, but once the wearable device is driven, it can automatically generate various types of additional information and provide them to a user. For example, if a user who has worn a wearable watch wants to measure his or her own heart rate, the wearable watch can measure the heart rate of the user as soon as the user presses a heart rate measurement input button, can generate various types of information based on the measured heart rate, and can provide them to the user. Recently, many wearable devices that do not need to be initially driven by user input are appearing. For example, a wearable band can continue to measure the heart rate of a user although it is not initially driven by user input. In the future, there is a very good possibility that a wearable device will be developed in such a way not to be initially driven by user input. The reason for this is that convenience in device driving is improved if user input is not required.

The origin of various types of additional information provided from such a wearable device to a user includes pieces of information measured from the user. For example, the pieces of information may include the heart rate, blood pressure, mental state, weight, body temperature, respiration volume, number of steps, matter of concern, current location, etc of a user. Accordingly, sensors for measuring various types of information from a user need to be mounted on a wearable device. The more the type of sensor is increased, the more information is measured from a user. Accordingly, a heart rate measurement sensor, a Global Positioning System (GPS) sensor and/or a number-of-steps measurement sensor tend to be essentially mounted on a recent wearable device. Research continues to be carried out to dispose various sensors in a limited space within a wearable device.

A wearable device can measure information from a user through sensors mounted thereon, can generate various types of additional information based on the measured information, and can provide them to the user. For example, if blood pressure of a user is too high as results of the measurement of the blood pressure, information about a medicine capable of lowering the blood pressure to a proper level may be provided to the user. Alternatively, the current location of the user may be measured, and information about a nearby store or commodities related to a matter of concern of the user may be provided to the user. Such additional information may be provided through a function embedded in a wearable device itself, but it is impossible for a single wearable device to provide all pieces of additional information to different users. Accordingly, recently, an application installed on a wearable device is also developed. In this case, the application may be considered to be a kind of application program, and may function to generate various types of additional information based on information measured through a function embedded in a wearable device itself and to provide them. In the above example, the provision of information about a medicine capable of lowering blood pressure to a proper level or information about a nearby store or commodities related to a matter of concern of a user can be provided by an application. That is, whenever a new application is developed, additional information which may be provided to a user through a wearable device is inevitably diversified. The development of an application may be considered to be a companion that steps forward along with the development of a wearable device itself.

The construction of a system capable of settlement through a wearable device is recently emerging as a main matter of concern in a related industry. For example, if a near field communication (NFC) function is included in a wearable device and a user's credit card is registered with an application, the user can perform settlement through the wearable device although the user does not take his or her purse out of his or her pocket. That is, a mobile wallet function can be performed by replacing a conventional wallet. However, there are many problems to be solved due to many problems related to security, such as personal information and the approval of credit card payment.

Furthermore, a conventional device for obtaining personal information using a wearable device, etc. is problematic in that the proportion of users who use the conventional device is decreased due to a feeling of resistance in a member subscription step.

Accordingly, an embodiment of the present invention proposes an apparatus for checking accurate authentication for a user and information about the body of the user by conveniently collecting information about the body composition of the user and authenticating veins of the user and for providing feedback to the user based on the results of the check.

The present invention has been invented based on such a technical background and also has been invented to satisfy the aforementioned technical needs and to provide additional technical elements that may not be easily invented by those skilled in the art to which the present invention pertains.

PRIOR ART DOCUMENT (Patent Document 1) KR 2015-0069086

SUMMARY OF THE INVENTION

An embodiment of the present invention is directed to identifying a user by sending previously stored personal information to a wearable device and to measuring a body composition of the user through the authenticating of veins of the user.

Furthermore, an embodiment of the present invention is directed to the provision of pieces of information about fitness equipment, sporting goods, food, and a coupon so that a user can have a desired amount of muscle, body fat and so on based on information, such as a body composition, the quantity of motion, etc. of the user.

Furthermore, an embodiment of the present invention is directed to enabling a user to frequently perform self-diagnosis conveniently without a burden regardless of sex or age so that the user can measure his or her body composition conveniently.

Furthermore, an embodiment of the present invention is directed to the provision of a payment service system and method using sharing payment means, which enable settlement to be performed through sharing payment means only when a predetermined condition is satisfied if the sharing payment means is used.

Furthermore, an embodiment of the present invention is directed to the proposal of a user authentication method of a new concept different from a conventional user authentication method using bio information, such as a face recognition, face contour recognition, fingerprint recognition, iris recognition, or vein recognition, by providing a user authentication device using a gait, thereby enabling user authentication even without a direct contact with a recognition device for checking bio information.

Furthermore, an embodiment of the present invention is directed to the provision of a real-time user authentication service using gait information.

Furthermore, an embodiment of the present invention is directed to the provision of a payment service system and method using sharing payment means, wherein settlement can be safely performed although a wearable device has been lost when the settlement is performed using the sharing payment means.

Furthermore, an embodiment of the present invention is directed to helping a user to keep a balanced body by checking the amount of action of each part of the body of the user, performing a comparison between the amounts of muscle and body fat of parts of the body, and notifying the user of an imbalanced body part through a convenient vein authentication procedure.

In an embodiment of the present invention, a wearable device for providing feedback information through vein authentication and the measurement of a body composition may include a measurement module configured to measure the pattern of veins and body composition of a user using a current, a communication module configured to send unique bio information about the user measured by the measurement module to a management server along with authentication information and to receive feedback information for the transmitted information from the management server, a control module configured to calculate a change of the body composition of the user or a movement of the user, and a memory module configured to store the pattern of the veins and body composition of the user.

Furthermore, the measurement module may include a photographing measurement device configured to include an infrared radiation device for measuring the pattern of the veins of the user by radiating infrared rays and a CCD camera, or a current measurement device configured to measure the pattern of the veins of the user by passing a fine current through the veins of the user.

Furthermore, the measurement module may notify the user whether the pattern of the veins measured by the measurement module is identical with a previously stored pattern of the veins of the user using the pattern of the veins measured by the measurement module.

Furthermore, the measurement module may include a current transmission device configured to measure the body composition of the user by passing a current through cells within the body of the user.

Furthermore, the measurement module may measure the amount of muscle or body fat of each part of the body of the user and notify the user of an imbalanced body part.

Furthermore, the feedback information may provide at least one of pieces of information about fitness equipment, sporting goods, food, and a coupon corresponding to body information about the body of the user.

In an embodiment of the present invention, a method for providing feedback information through vein authentication and the measurement of a body composition may include a wearing step for wearing, by a user, a wearable device on his or her body, a vein information acquisition step for obtaining, by the wearable device, vein information using a photographing measurement device including an infrared radiation device and a CCD camera or a current measurement device, a vein authentication step for identifying the user by comparing the vein information obtained at the vein information acquisition step with existing vein information, a communication step for sending unique bio information about the user obtained at the vein information acquisition step to a management server along with authentication information and receiving feedback information for the transmitted information from the management server, a storage step for storing contents at the vein information acquisition step, the vein authentication step, and the communication step in the wearable device, and a service providing step for measuring a body composition of the user by passing a current through cells within the body and providing at least one of pieces of information about fitness equipment, sporting goods, food, and a coupon corresponding to body information about the body of the user.

Furthermore, the vein authentication step may include an initial input step for setting a pattern of the veins of the user, a vein pattern reception step for receiving a pattern of the veins obtained in real time when the user uses the wearable device, and an authentication step for identifying the user by comparing the pattern of the veins inputted at the initial input step with the pattern of the veins obtained in real time.

Furthermore, the communication step may include the steps of receiving the vein information obtained at the vein information acquisition step, receiving the authentication information obtained through the identification of the user and the comparison at the vein authentication step, and sending, by a communication module, the obtained vein information and authentication information to the management server and receiving the feedback information for the transmitted information from the management server.

Furthermore, the communication step may include storing, by the database of the management server, user information or the feedback information, receiving, by the server communication unit of the management server, the obtained vein information and authentication information of the user from the wearable device, selecting, by the server control unit of the management server, feedback information from a database based on the received vein information and authentication information, and sending, by the server communication unit of the management server, the information selected by the server control unit to the wearable device.

Furthermore, the service providing step may include the steps of measuring the body composition or movement of the user by passing a current through cells within the body, calculating a change of the body composition or movement of the user, and sending, by a communication module, information about the measured body composition or measured quantity of motion to the management server and receiving feedback information for the transmitted information from the management server.

In addition, the service providing step may include the steps of storing, by the database of the management server, user information or feedback information, receiving, by the server communication unit of the management server, information about the body composition or quantity of motion measured by the wearable device, selecting, by the server control unit of the management server, feedback information from the database based on the received information about the body composition or quantity of motion, and sending, by the server communication unit of the management server, the information selected by the server control unit to the wearable device.

In accordance with an aspect of the present invention, there is provided a wearable device, including a short-range communication unit configured to sense at least one wearable device in a short distance, a user authentication unit configured to authenticate a user of the sensed wearable device, and a control unit configured to send a first authentication token to the wearable device sensed through the short-range communication unit if the user has been authenticated and to activate sharing payment means with the sensed wearable device if a second authentication token received from the sensed wearable device is valid.

The first authentication token or the second authentication token may include a previously stored token or a newly generated token, and may include user ID information or an expiration date.

The control unit may perform pairing with the sensed wearable device if the second authentication token is valid, may check the sharing payment means with the sensed wearable device, and may activate the sharing payment means if an activation condition of the sharing payment means is satisfied.

The control unit may perform settlement using the activated sharing payment means.

The wearable device may further include a storage unit configured to store reference authentication information, information about sharing payment means shared with each wearable device, and an activation condition for activating the sharing payment means.

In accordance with an aspect of the present invention, there is provided a method for providing, by a wearable device, a payment service using sharing payment means, including the steps of (a) authenticating a user and obtaining or generating a first authentication token, (b) sending the obtained or generated first authentication token to at least one wearable device sensed through short-range communication, (c) receiving a second authentication token from the sensed wearable device and determining whether the second authentication token is valid or not, and (d) activating sharing payment means shared with the sensed wearable device if the second authentication token is valid.

The step (a) may include the steps of obtaining bio information about the user, determining whether the obtained bio information is identical with previously stored bio information by comparing the obtained bio information with the previously stored bio information, and obtaining the previously stored first authentication token or generating the first authentication token if, as a result of the determination, it is determined that the obtained bio information is found to be identical with the previously stored bio information.

The step (d) may include the steps of performing pairing with the sensed wearable device if the second authentication token is valid, checking the sharing payment means shared with the sensed wearable device, determining whether an activation condition of the sharing payment means is satisfied, and activating the sharing payment means if the activation condition is satisfied.

In accordance with another aspect of the present invention, there is provided a method for providing, by a wearable device, a payment service using sharing payment means, including the steps of (a) authenticating a user and obtaining or generating a first authentication token, (b) sending the obtained or generated first authentication token to at least one wearable device sensed through short-range communication, and (c) receiving a second authentication token from the sensed wearable device and sending the first and the second authentication tokens to a user device paired with the wearable device.

The user device may determine whether the first or second authentication token is valid or not, may check sharing payment means shared with the sensed wearable device if, as a result of the determination, the first or second authentication token is valid, and may activate the sharing payment means if an activation condition of the sharing payment means is satisfied.

In an embodiment of the present invention, an apparatus for providing a user authentication service is based on a smart device, and may include a sensing unit configured to sense gait information about the gait of a user, an information storage unit configured to store the sensed gait information, a data transmission unit configured to send the gait information stored in the information storage unit to a central management server, a data reception unit configured to receive user authentication information returned by the central management server, and a display unit configured to display the user authentication information received by the data reception unit on a screen.

In accordance with an embodiment of the present invention, the sensing unit may sense the gait information of the user using any one of a terrestrial magnetic sensor, a gyro sensor, and an acceleration sensor.

In accordance with an embodiment of the present invention, the apparatus may further include a conversion unit configured to pattern the sensed gait information.

In accordance with an embodiment of the present invention, the central management server may be associated with the smart device through wired/wireless communication, and may include an integration reception unit configured to receive the gait information from the data transmission unit, a comparison unit configured to compare the gait information received from the data transmission unit with previously stored user information, and an integration transmission unit configured to send the user authentication information to the data reception unit.

In accordance with an embodiment of the present invention, the data reception unit may further receive digital content from the central management server or a content providing server. The display unit may display the digital content received by the data reception unit on a screen.

In accordance with an embodiment of the present invention, the apparatus may further include a correction unit configured to correct the sensed gait information with respect to a variable value according to the geographic features of a footpath.

In accordance with an embodiment of the present invention, the gait information may be obtained using global positioning systems (GPS) or obtained by receiving a signal from an action sensing unit attached to a shoe or body of the user for gait tracking.

In accordance with an embodiment of the present invention, the gait information may be obtained using at least one of a value calculated by measuring the moving distance of the user per hour, the stride of the user, and the foot angle, toe-out angle, and walking frequency of the user upon walking.

In accordance with an embodiment of the present invention, there is provided a method for providing a user authentication service based on a smart device. The method may include the steps of sensing gait information about the gait of a user, storing the sensed gait information, sending the gait information to a central management server using a data transmission unit; receiving user authentication information through a data reception unit, and displaying the received user authentication information on a screen.

In this case, the method may further include the step of patterning the sensed gait information.

The method may further include the step of switching to user-customized service data using the user authentication information.

Furthermore, the method may further include sensing gait information about the gait of the user in real time, comparing the sensed real-time gait information with user information for a set time even after user authentication is completed, and receiving updated user authentication information.

DETAILED DESCRIPTION

Figure 1:
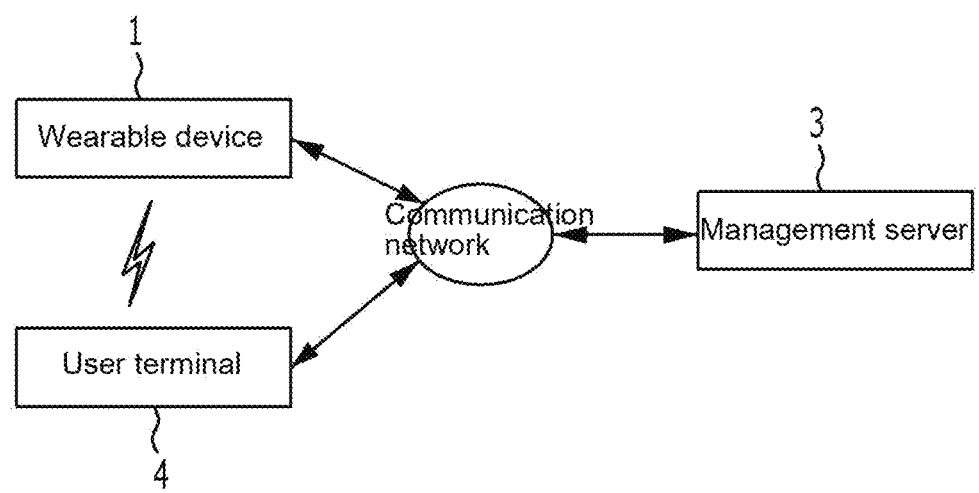
FIG. 1 is a diagram showing association between a wearable device for providing feedback information through vein authentication and the measurement of a body composition, a management server, etc. according to an embodiment of the present invention.

Hereinafter, some embodiments of the present invention are described in detail with reference to the exemplary drawings. The embodiments are provided so that those skilled in the art may easily understand the technical spirit of the present invention and the present invention is not restricted by the embodiments. A detailed description of the known functions and constructions will be omitted if it is deemed to make the gist of the present invention unnecessarily vague. The details of the objects and technical configurations of the present invention and acting effects thereof will be more clearly understood from the following detailed description based on the accompanying drawings. Hereinafter, embodiments of the present invention are described in detail with reference to the accompanying drawings.

Embodiments disclosed in this specification should not be interpreted as limiting or used to limit the scope of the present invention. It is evident to those skilled in the art that a description including the embodiments of this specification has various applications. Accordingly, unless otherwise defined by the claims, some embodiments described are illustrative for better understanding, and the scope of the present invention is not intended to be restricted by the embodiments.

Function blocks illustrated in the drawings and described hereunder are only examples of possible implementations. In other implementations, different functional blocks may be used without departing from the spirit and scope of the detailed description. Furthermore, one or more functional blocks of the present invention are illustrated as separate blocks, but one or more of the functional blocks of the present invention may be a combination of various hardware and software elements for executing the same function.

Furthermore, it should be understood that an expression that some elements are "included" is an expression of an "open type" and the expression simply denotes that the corresponding elements are present, but does not exclude additional elements. Furthermore, contents represented in the accompanying drawings have been diagrammed in order to easily describe the embodiments of the present invention, and the contents may be different from drawing forms that are actually implemented. It is to be noted that in assigning reference numerals to elements in the drawings, the same reference numerals denote the same elements throughout the drawings even in cases where the elements are shown in different drawings.

Furthermore, when it is said that one element is "connected" or "coupled" to the other element, it should be understood that one element may be directly "connected or coupled" to the other element, but a third element may exist between the two elements.

Furthermore, expressions, such as "the first" and "the second", are expressions used to only distinguish a plurality of elements from one another, and do not limit the sequence of the elements or other characteristics.

FIG. 1 is a diagram showing association between a wearable device for providing feedback information through vein authentication and the measurement of a body composition, a management server, etc. according to an embodiment of the present invention.

Referring to FIG. 1, a system for providing feedback information through vein authentication and the measurement of a body composition according to an embodiment of the present invention includes a wearable device 1 and a management server 3. More specifically, the system may include the wearable device 1 configured to measure a vein, body composition or movement of a user, terminate an authentication procedure by identifying the user based on the measured vein of the user, calculate the quantity of motion of the user based on the body composition and movement, send information about the measured body composition or quantity of motion to the management server 3, and receive feedback information for the transmitted information from the management server 3 and the management server 3 configured to store and update user information or feedback information, receive information about the body composition or the quantity of motion measured by the wearable device 1, select feedback information from a database based on the received information about the body composition or the quantity of motion, and send the selected feedback information to the wearable device 1.

The wearable device 1 may include a measurement module 11 configured to measure the pattern of veins and the body composition of a user using an electric current, a communication module 12 configured to send unique bio information about the user, measured by the measurement module, to the management server along with authentication information and receive feedback information for the transmitted information from the management server, a control module 13 configured to calculate a change in the body composition of the user or a movement of the user, and a memory module 14 configured to store the pattern of the veins, body composition, etc. of the user.

In an embodiment of the present invention, the characteristics of the hematocele of veins of a user is checked by flowing an electric current into the vein of the user through the wearable device 1, and whether the user is a user who uses corresponding syrup is checked by performing a comparison and authentication on the user and the user who uses corresponding syrup.

Accordingly, syrup can be immediately used without a need for a separate membership subscription procedure.

In a detailed embodiment, a user performs common authentication through a mobile service. When the authentication is completed, the wearable device 1 is aware that the authentication has been completed in a mobile.

Furthermore, the wearable device 1 obtains unique bio information about a user through veins of the user at a corresponding point of time, and sends the corresponding information to a server along with encrypted authentication information stored in the mobile.

Furthermore, the server receives a corresponding value, confirms that the user is what user by decrypting the encrypted authentication information, and stores digitized bio information in a corresponding user authentication table.

Thereafter, although a mobile service has been deleted, an app is authenticated without a separate login because vein authentication is performed through the wearable device 1 when the app is reinstalled.

In this case, if the same authentication information is used by a different service, the different service may be used through vein authentication without separate authentication.

The wearable device 1 literally refers to a device which may be worn on the human body, and includes various types of devices, such as glasses, a watch, a bracelet, shoes, a ring, a belt, a band, a necklace, a headset, and clothing, depending on a part on which the device is worn.

In an embodiment of the present invention, the wearable device 1 may measure a vein, a body composition, and the quantity of motion of a user. The body composition includes the weight, body water, protein, inorganic matter, body fat, skeletal muscle mass, Body Mass Index (BMI), body fat rate, abdominal obesity rate, diagnosis of obesity, amount of fat control, amount of muscle control, recommended exercise, physical development index, basal metabolic rate, evaluation of body fat for each part, evaluation of muscle development for each part, a body balance, etc. of the human.

In this case, the wearable device 1 includes an electrode, and may use the principle that an electric current well flows into a muscle containing much water and rarely flows into fat less containing water when the electric current flows into the body of a user. Accordingly, a body composition may be measured in such a way as to measure body water, protein, an inorganic matter, and fat, that is, compositions forming the human body, by measuring a resistance value (impedance) which is generated when a fine current passes through the human body. Such a measurement of the body composition is only an example, and the body composition may be measured in various ways using the wearable device 1.

Furthermore, a conventional device for measuring information about exercise of a user using the wearable device 1, etc. has a problem in that the same results are obtained if any user takes exercise and thus has a problem in that an accurate quantity of motion cannot be measured by incorporating information about the body of each user.

In contrast, the wearable device 1 according to an embodiment of the present invention can calculate an accurate quantity of motion of each user by analyzing a body composition and motion of the user, and can receive corresponding feedback from the management server 3 based on the body composition and quantity of motion of the user.

For example, as the results of the analysis of a user's body composition through the wearable device 1, if the user has height of 170 cm, weight of 90 kg, a body fat rate of 30%, an abdominal obesity rate of 10%, and a basal metabolic rate of 2700 kcal, the quantity of 1-day motion including a breast part of 100 kcal and a wrist part of 40 kcal through a user's motion may be measured based on the body composition by measuring the results of the 1-day motion and exercise. Accordingly, when such results of the measurement are transmitted to the management server 3, the management server 3 may send feedback information suitable for the user to the wearable device 1, so the user can obtain various types of information suitable for him or her.

The management server 3 may feed feedback information, more specifically, fitness equipment information, sporting goods information, food information, a coupon information, etc. suitable for a user back to the user based on information about the body composition and quantity of motion of the user received from the wearable device 1.

For example, if the body composition of a user received from the wearable device 1 includes height of 170 cm, weight of 90 kg, a body fat rate of 30%, an abdominal obesity rate of 10%, and a basal metabolic rate of 2700 kcal, a received quantity of 1-day motion is a breast part of 100 kcal, and a wrist part 40 of kcal, the management server 3 may provide information about a part that requires more exercise, fitness equipment or an exercise method for the exercise of the part, sporting goods recommended to protect a joint if the user is obesity, food to be eaten and food to be avoided by the user, and stores and a coupon in which the commodities are handled based on information transmitted by the user.

The wearable device 1 or a user terminal 300 to be described later and the management server 3 may be connected over wired/wireless communication networks. The communication network includes a base station controller, a base station transmitter, a relay station and so on. In this case, the base station controller functions to relay a signal between the base station transmitter and a switching station. The communication network supports both a synchronous method and an asynchronous method. Accordingly, in the case of the synchronous method, a Base Station Transmission System (BTS) may become a transmission/reception base station transmitter and a Base Station Controller (BSC) may become a transmission/reception base station controller. In the case of the asynchronous method, a Radio Transceiver Subsystem (RTS) may become the transmission and reception base station transmitter, and a Radio Network Controller (RNC) may become the transmission and reception base station controller. The communication network according to an embodiment of the present invention is not limited thereto, and may collectively refer to a GSM network other than a CDMA network and networks which may be used in the access network of a next-generation mobile communication system to be developed in the future.

The communication network may further include an access point. The access point is a small base station, such as a femto or pico base station chiefly installed in a building. The femto or pico base station is classified depending on how many the wearable devices 1 or a user terminal 4 can be accessed in terms of the classification of a small base station. Furthermore, the access point includes a short-range communication module for performing short-range communication, such as Wi-Fi, along with the wearable device 1 or the user terminal 4. The short-range communication may be performed in accordance with various standards, such as Bluetooth communication, Zigbee communication, infrared rays communication (IrDA), a Radio Frequency (RF) including a Ultra High Frequency (UHF) and a Very High Frequency (VHF), and ultra-wideband communication (UWB), in addition to Wi-Fi. The access point may extract the location of a data packet, may designate the best communication route for the extracted location, and may transfer the data packet to a next device, for example, the wearable device 1 or the user terminal 4 along the designated communication route. The access point may be shared by several lines in a common network environment.

The access point is basically divided into a fixed type access point and a mobile type access point. The fixed type access point may include a router, a repeater, a relay station and so on. The mobile type access point may include the bridge product of a specific manufacturer, such as KT's Egg. Such a mobile type access point may read a reception-side address from transmission-side information while guaranteeing free mobility, may designate the most appropriate communication route, and may send data.

In another embodiment of the present invention, the system for measuring a body composition and providing feedback information may further include the user terminal 4 configured to store information about a body composition and the quantity of motion measured by the wearable device 1 or feedback information received from the management server and to output the information.

Accordingly, in an embodiment of the present invention, since the wearable device 1 and the management server 3 operate in conjunction with each other even along with the user terminal 4, information about a body composition or the quantity of motion is provided to a user although the user has not worn the wearable device 1. Accordingly, the user can make a plan for his or her exercise while not taking exercise, can receive feedback information from the management server 3, and can easily access several commodities.

The user terminal 4 includes a Personal Digital Assistant (PDA), a smart phone, a cellular phone, a Personal Communication Service (PCS) phone, a Global System for Mobile (GSM) phone, a Wideband CDMA (W-CDMA) phone, a CDMA-2000 phone, a Mobile Broadband System (MSB) phone, etc. which may be applied to various wired/wireless environments. In this case, the user terminal 4 may refer to a portable small-sized device, but may also be called a mobile communication terminal if it includes a camcorder, a laptop computer or the like. In an embodiment of the present invention, the user terminal 4 is not specifically limited thereto.

In another embodiment of the present invention, the measurement module 11 of the wearable device 1 for providing feedback information through vein authentication and the measurement of a body composition may include a photographing measurement device 111 configured to include an infrared radiation device for measuring the pattern of veins of a user by radiating infrared rays and a CCD camera or a current measurement device 112 configured to measure the pattern of veins of a user by passing a fine current through the vein of the user.

Figure 2:
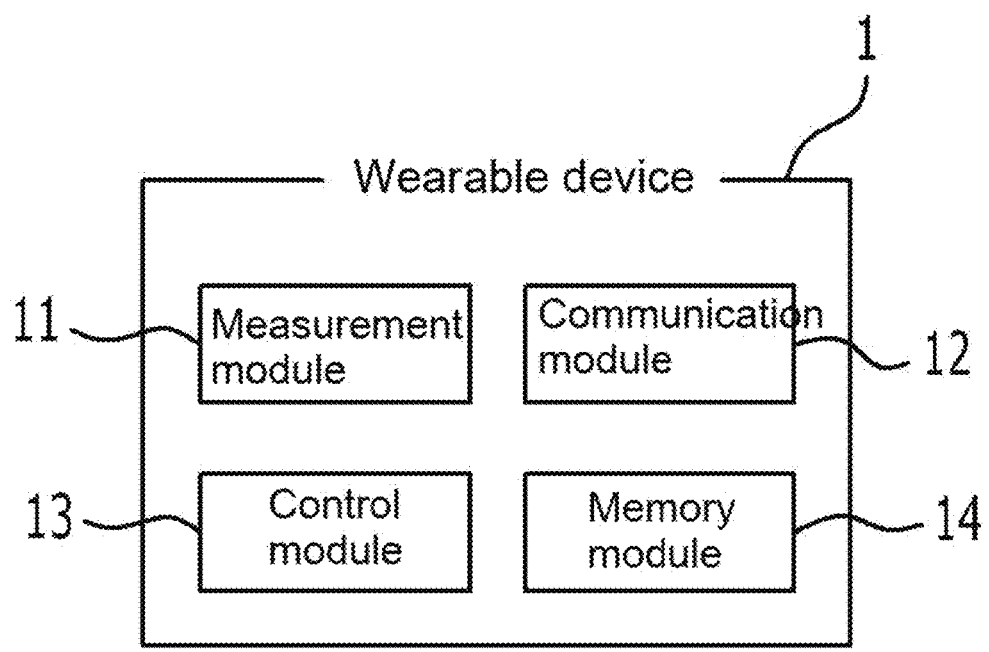
FIG. 2 is a functional block diagram of the wearable device for providing feedback information through vein authentication and the measurement of a body composition according to an embodiment of the present invention.

FIG. 2 is a functional block diagram of the wearable device for providing feedback information through vein authentication and the measurement of a body composition according to an embodiment of the present invention.

Figure 3:
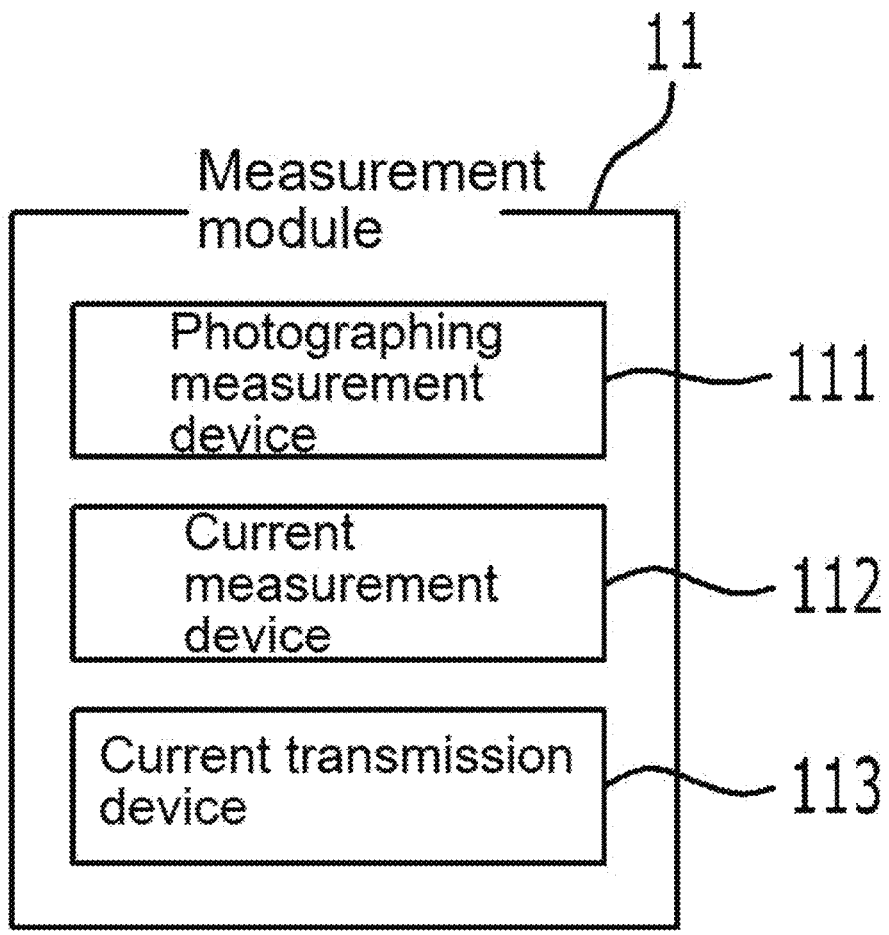
FIG. 3 is a functional block diagram of the measurement module of the wearable device for providing feedback information through vein authentication and the measurement of a body composition according to an embodiment of the present invention.

FIG. 3 is a functional block diagram of the measurement module of the wearable device for providing feedback information through vein authentication and the measurement of a body composition according to an embodiment of the present invention.

From FIGS. 2 and 3, it may be seen the functional blocks including the wearable device 1 and the elements included in the measurement module.

The photographing measurement device 111 of the measurement module 11 includes the infrared radiation device and the CCD camera. The photographing measurement device 111 photographs veins at any place of the wrist of a user, the back of the hand of the user, and the palm of the hand of the user using infrared rays and identifies the user by checking the pattern of the veins.

Furthermore, the current measurement device 112 of the measurement module 11 flows a fine current into veins of a user so that the wearable device 1 can check the configuration of the veins of the user.

Furthermore, in another embodiment of the present invention, the measurement module 11 may include a current transmission device 113 configured to measure a body composition of a user by passing an electric current through cells within the body.

Accordingly, the measurement module 11 measures a body composition or motion of a user. In this case, the body composition includes the weight, body water, protein, inorganic matter, body fat, skeletal muscle mass, Body Mass Index (BMI), body fat rate, abdominal obesity rate, diagnosis of obesity, amount of fat control, amount of muscle control, recommended exercise, physical development index, basal metabolic rate, evaluation of body fat for each part, evaluation of muscle development for each part, a body balance, etc. of the human.

In this case, the measurement module 11 may be attached to any part of the human body or may be attached to a plurality of parts. The measurement module includes an electrode, and may use the principle that an electric current well flows into a muscle containing much water and rarely flows into fat less containing water when the electric current flows into the body of a user. Accordingly, a body composition may be measured in such a way as to measure body water, protein, an inorganic matter, and fat, that is, compositions forming the human body, by measuring a resistance value (impedance) which is generated when a fine current passes through the human body. Such a measurement of the body composition is only an example, and the body composition may be measured in various principles.

In another embodiment of the present invention, the measurement module 11 may include a body composition measurement sensor and a motion sensor. The body composition measurement sensor may measure information about a body composition, such as the weight, body water, protein, inorganic matter, body fat, skeletal muscle mass, Body Mass Index (BMI), body fat rate, abdominal obesity rate, diagnosis of obesity, amount of fat control, amount of muscle control, recommended exercise, physical development index, basal metabolic rate, evaluation of body fat for each part, evaluation of muscle development for each part, and a body balance of the human, by measuring a resistance value generated when a fine current flows into the body of the human. The motion monitoring sensor may measure motion information, such as a muscle motion, heartbeat, and the respiration volume of a user.

In a conventional method for measuring a body composition, a weight scale type device measures a body composition through the electrodes of feet, but various embodiments according to the location of the measurement module 11 of the wearable device 1 of the present invention are as follows.

<Embodiments According to the Location of the Measurement Module 11>

1) Measurement of Body Composition and Motion Through a Patch Type Wearable Device 1

The body composition measurement sensor of the wearable device 1 attached to part of the body in a patch form may measure a body composition. The motion sensor embedded in the wearable device 1 may measure a motion.

2) Measurement of Body Composition and Motion Through a Breast Belt Type Wearable Device 1

The body composition measurement sensor of the breast belt type wearable device 1 configured to have a form of clothes, such as T-shirts, and attached to surround the breast may measure a body composition. The motion sensor embedded in the wearable device 1 may measure a motion.

3) Measurement of Body Composition and Motion Through a Wrist Type Wearable Device 1

The body composition measurement sensor of the wrist type wearable device 1, such as a smart watch or a smart band, may measure a body composition. The motion sensor embedded in the wearable device 1 may measure a motion.

4) Measurement of Body Composition and Motion Through a Wrist Wearable Device 1

The body composition measurement sensor of the wrist wearable device 1 having a form capable of being wound on a wrist may measure a body composition. The motion sensor embedded in the wearable device 1 may measure a motion.

5) Measurement of Body Composition and Motion Through a Whole Body Type Wearable Device 1

The body composition measurement sensor of the wearable device 1 having a clothing form closely attached to the whole body of a user may measure a body composition. The motion sensor embedded in the wearable device 1 may measure a motion.

The aforementioned embodiments of the measurement module are not intended to limit embodiments of the present invention to the proposed forms. Accordingly, those skilled in the art to which the present invention pertains may alter, change, and modify the embodiments without departing from the scope of the present invention.

Furthermore, in another embodiment of the present invention, the measurement module 11 may measure the amount of muscle or body fat of each part of a user and notify the user of a unbalanced part. The measurement module may check the amount of muscle or body fat of each part which belongs to information about the body composition of the human body, may check the amount of activity of each part based on the amount of muscle or body fat, may perform a comparison on the amounts of muscles and body fat of the parts, and may notify the user of a unbalanced part in order to help the user to keep a balanced body.

Furthermore, the measurement module 11 may provide notification of whether the previously stored pattern of veins of a user is identical with the pattern of the veins of the user measured by the measurement module 11.

Furthermore, the measurement module 11 may measure the amount of muscle or body fat of each part of the body of a user and notify the user of an imbalanced body part. The feedback information may provide at least one of pieces of information about fitness equipment, sporting goods, food, and a coupon corresponding to information about the body of a user.

Furthermore, the control module 13 may calculate the quantity of motion attributable to a motion of a user by incorporating information about a body composition measured by the measurement module 11. In particular, the control module 13 may calculate the quantity of motion by taking into consideration information about at least one of the height, weight, body composition, and sex of the user.

For example, as the results of the analysis of a user's body composition through the measurement module 11, if the user has height of 170 cm, weight of 90 kg, a body fat rate of 30%, an abdominal obesity rate of 10%, and a basal metabolic rate of 2700 kcal, the quantity of 1-day motion including a breast part of 100 kcal and a wrist part of 40 kcal through a user's movement may be measured based on the body composition by measuring the results of the 1-day movement and exercise. Accordingly, when such results of the measurement are transmitted to the management server 3, the management server 3 may send feedback information suitable for the user to the wearable device 1, so the user can obtain various types of information suitable for him or her.

In this case, the feedback information may include at least one of pieces of information about fitness equipment, sporting goods, food, and a coupon corresponding to information about the body of a user. More specifically, the feedback information includes information about a part that requires more exercise, fitness equipment or an exercise method for the exercise of the part, sporting goods recommended to protect a joint if the user is obesity, food to be eaten and food to be avoided by the user, and stores and a coupon in which the commodities are handled based on information transmitted by the user.

The communication module 12 sends information about the measured body composition or quantity of motion to the management server over a communication network, and receives feedback information for the transmitted information from the management server. In this case, the communication network includes both wired and wireless communication, and the wearable device 1 for measuring a body composition and providing feedback information and the management server 3 for measuring a body composition and providing feedback information are interconnected over a communication network.

The management server 3 for measuring a body composition and providing feedback information according to an embodiment of the present invention may include a database, a server communication unit, and a server control unit. More specifically, the management server 3 may include the database configured to store and update user information or feedback information, the server communication unit configured to receive information about the body composition or quantity of motion of a user measured by the wearable device 1 and to send information selected by the control unit to the wearable device 1, and the server control unit configured to select feedback information from the database based on the received information about the body composition or quantity of motion.

The database may store information received from the wearable device 1, such as user information (e.g., information about the age, sex, height, weight, and body fat of a user and physical measured values required by the user), pieces of information about fitness equipment, sporting goods, food, and a coupon, and feedback information to be provided to a user, and may update information when new information is received from the wearable device 1 or the external apparatus. In this case, the database is a device for storing data, and basically stores data, such as environment variables for searth, classification, and analysis. Such a function of the database may be implemented using a known technology, and thus a detailed description of an implementation is omitted.

The server control unit may select feedback information from the database based on received information about a body composition or the quantity of motion. For example, the database stores different information according to the physical constitution and weight of each person. If a body composition of a user received from the wearable device 1 includes height of 170 cm, weight of 90 kg, a body fat rate of 30%, an abdominal obesity rate of 10%, and a basal metabolic rate of 2700 kcal, the server control unit may determine the physical constitution or weight group of the user, and may extract food to be avoided by the user, weight to be reduced for normal weight, a distance that the user needs to walk for a day, calories to be consumed for a day, food to be eaten for a day, food to be avoided by the user if the user is obesity, etc. from the database.

In this case, the server control unit may recommend at least one of suitable food, fitness equipment, and sporting goods based on current information about the body of a user so that the user can reach a predetermined target body measurement value. For example, if information about the quantity of motion received from the wearable device 1 includes that the quantity of 1-day motion of a user is a breast part of 100 kcal and a wrist part of 40 kcal, the server control unit may provide information about a part that requires more exercise, fitness equipment or an exercise method for the exercise of the part, sporting goods recommended to protect a joint if the user is obesity, food to be eaten and food to be avoided by the user, and stores and a coupon in which the commodities are handled.

In addition, the server control unit may update information about a user's body composition in real time whenever it receives information about a user's body composition from the wearable device 1. Accordingly, a user can easily check a change of his or her body and required information depending on the quantity of motion daily without a need to write his or her body information separately.

The server communication unit may receive information about the body composition or quantity of motion of a user measured by the wearable device 1 over a communication network, and may send information selected by the server control unit to the wearable device 1. In this case, the communication network includes both wired and wireless communications, and the wearable device 1 for measuring a body composition and providing feedback information and the management server 3 for measuring a body composition and providing feedback information are interconnected over a communication network.

Figure 4:
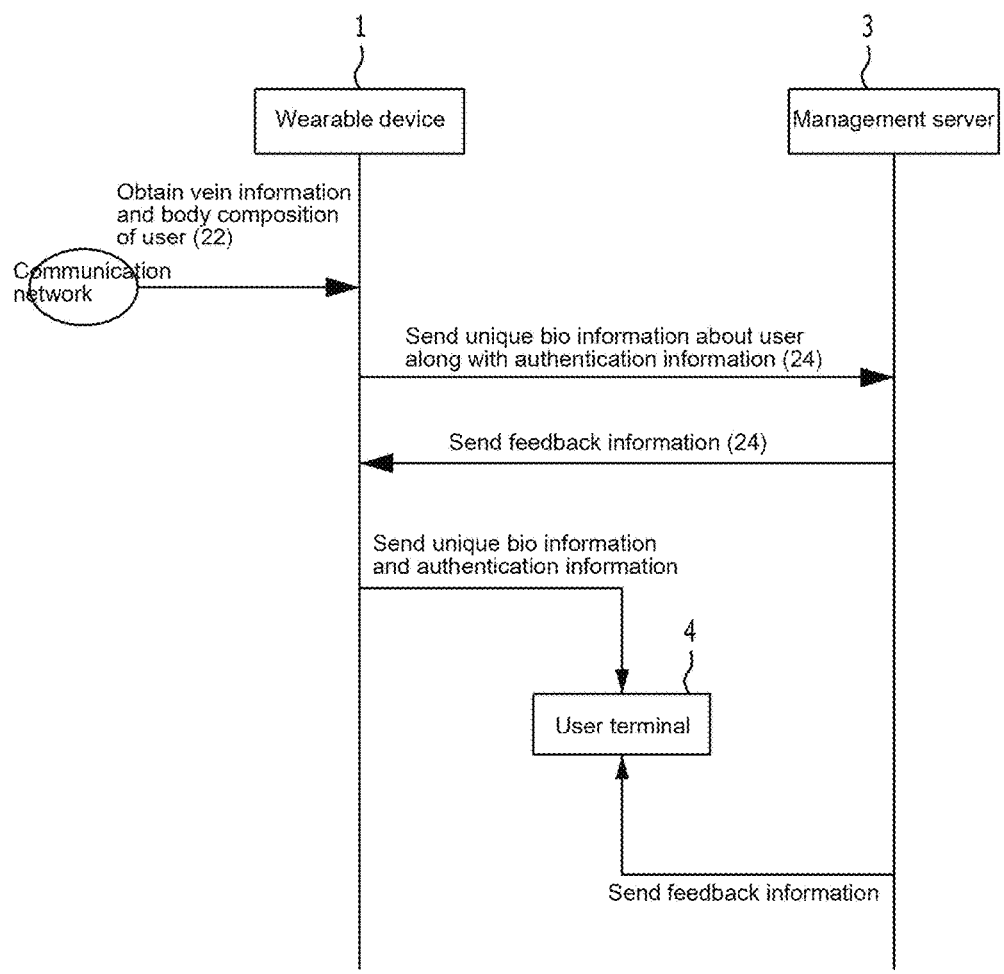
FIG. 4 is a diagram showing association between the wearable device for providing feedback information through vein authentication and the measurement of a body composition, the management server, etc. according to an embodiment of the present invention.

FIG. 4 is a diagram showing association between the wearable device 1 for providing feedback information through vein authentication and the measurement of a body composition, the management server 3, etc. according to an embodiment of the present invention.

Referring to FIG. 4, the provision of feedback information through vein authentication and the measurement of a body composition according to an embodiment of the present invention includes (a) step 22 for obtaining information about a vein and body composition of a user, (b) a communication step 24 for sending, by the wearable device, the measured unique bio information about the user to the management server along with authentication information, and (c) a communication step 24 for selecting, by the management server, feedback information from the database based on received information about the body composition or the quantity of motion and sending the feedback information to the wearable device.

The wearable device 1 literally refers to a device which may be worn on the human body, and includes various types of devices, such as glasses, a watch, a bracelet, shoes, a ring, a belt, a band, a necklace, a headset, and clothing, depending on a part on which the device is worn.

At step (a), the wearable device 1 includes an electrode, and may measure a body composition using the principle that an electric current well flows into a muscle containing much water and rarely flows into fat less containing water when the electric current flows into the body of a user. Accordingly, the wearable device 1 may measure a body composition in such a way as to measure body water, protein, an inorganic matter, and fat, that is, compositions forming the human body, by measuring a resistance value (impedance) which is generated when a fine current passes through the human body. Such a measurement of the body composition is only an example, and the body composition may be measured in various ways using the wearable device 1.

In this case, the body composition includes the weight, body water, protein, inorganic matter, body fat, skeletal muscle mass, Body Mass Index (BMI), body fat rate, abdominal obesity rate, diagnosis of obesity, amount of fat control, amount of muscle control, recommended exercise, physical development index, basal metabolic rate, evaluation of body fat for each part, evaluation of muscle development for each part, a body balance, etc. of the human.

Furthermore, a conventional device for measuring information about exercise of a user using the wearable device 1, etc. has a problem in that the same results are obtained if any user takes exercise and thus has a problem in that an accurate quantity of motion cannot be measured by incorporating information about the body of each user.

However, the wearable device 1 according to an embodiment of the present invention may calculate an accurate quantity of motion of each user by analyzing the body composition and motion of the user as at step (a), and may receive corresponding feedback from the management server 3 based on the body composition and quantity of motion of the user.

At step (b), the wearable device 1 calculates the quantity of motion based on the measured motion of the user, and sends information about the measured body composition or quantity of motion to the management server.

For example, as the results of the analysis of a user's body composition through the wearable device 1, if the user has height of 170 cm, weight of 90 kg, a body fat rate of 30%, an abdominal obesity rate of 10%, and a basal metabolic rate of 2700 kcal, the quantity of 1-day motion including a breast part of 100 kcal and a wrist part of 40 kcal through a user's motion may be measured based on the body composition by measuring the results of the 1-day motion and exercise. Accordingly, when such results of the measurement are transmitted to the management server 3, the management server 3 may send feedback information suitable for the user to the wearable device 1, so the user can obtain various types of information suitable for him or her.

At step (c), the management server 3 receives information about the measured body composition or quantity of motion of the user from the wearable device 1. At step (c), the management server 3 selects feedback information from the database based on the received information about the body composition or quantity of motion, and sends the feedback information to the wearable device 1. The management server 3 may feed feedback information suitable for the user, more specifically, information about fitness equipment, sporting goods, food, and a coupon back to the user based on the information about the body composition and quantity of motion received from the wearable device 1.

For example, if the body composition of a user received from the wearable device 1 includes height of 170 cm, weight of 90 kg, a body fat rate of 30%, an abdominal obesity rate of 10%, and a basal metabolic rate of 2700 kcal, a received quantity of 1-day motion is a breast part of 100 kcal, and a wrist part 40 of kcal, the management server 3 may provide information about a part that requires more exercise, fitness equipment or an exercise method for the exercise of the part, sporting goods recommended to protect a joint if the user is obesity, food to be eaten and food to be avoided by the user, and stores and a coupon in which the commodities are handled.

Accordingly, the wearable device 1 receives the feedback information from the management server. The feedback information includes at least any one of user information, pieces of information about fitness equipment, sporting goods, food, and a coupon.

The wearable device 1 or the user terminal 4 and the management server 3 may be connected over a wired or wireless communication network. The communication network includes a base station controller, a base station transmitter, a relay station and so on. In this case, the base station controller functions to relay a signal between the base station transmitter and a switching station. The communication network supports both a synchronous method and an asynchronous method. Accordingly, in the case of the synchronous method, a Base Station Transmission System (BTS) may become a transmission/reception base station transmitter and a Base Station Controller (BSC) may become a transmission/reception base station controller. In the case of the asynchronous method, a Radio Transceiver Subsystem (RTS) may become the transmission and reception base station transmitter, and a Radio Network Controller (RNC) may become the transmission and reception base station controller. The communication network according to an embodiment of the present invention is not limited thereto, and may collectively refer to a GSM network other than a CDMA network and networks which may be used in the access network of a next-generation mobile communication system to be developed in the future.

The communication network may further include an access point. The access point is a small base station, such as a femto or pico base station chiefly installed in a building. The femto or pico base station is classified depending on how many the wearable devices 1 or the user terminal 4 can be accessed in terms of the classification of a small base station. Furthermore, the access point includes a short-range communication module for performing short-range communication, such as Wi-Fi, along with the wearable device 1 or the user terminal 4. The short-range communication may be performed in accordance with various standards, such as Radio Frequencies (RF) and a ultra-wideband communication (UWB) including Bluetooth communication, Zigbee communication, infrared rays communication (IrDA), a Ultra High Frequency (UHF), and a Very High Frequency (VHF), in addition to Wi-Fi. The access point may extract the location of a data packet, may designate the best communication route for the extracted location, and may transfer the data packet to a next device, for example, the wearable device 1 or the user terminal 4 along the designated communication route. The access point may be shared by several lines in a common network environment.

The access point is basically divided into a fixed type access point and a mobile type access point. The fixed type access point may include a router, a repeater, a relay station and so on. The mobile type access point may include the bridge product of a specific manufacturer, such as KT's Egg. Such a mobile type access point may read a reception-side address from transmission-side information while guaranteeing free mobility, may designate the most appropriate communication route, and may send data.

In another embodiment of the present invention, the system for measuring a body composition and providing feedback information may further include the user terminal 4 configured to store information about a body composition and the quantity of motion measured by the wearable device 1 or feedback information received from the management server and to output the information.

In another embodiment of the present invention, the service providing method may further include updating, by the management server, information about the body composition of each user in real time whenever it receives information about the body composition of the user from the wearable device 1.

In this case, updating the information is possible at any time without being limited to a time-series sequence.

The service providing method may further include may further include sending, by the wearable device 1, information about the measured body composition and quantity of motion to the user terminal 4 and sending, by the management server, the feedback information to the user terminal 4 so that even the user terminal 4 operates in conjunction with the wearable device 1 and the management server. Accordingly, a user can make a plan for his or her exercise while not taking exercise, can receive feedback information from the management server 3, and can easily access several commodities because information about a body composition or quantity of motion is provided to the user while the user does not wear the wearable device 1.

The user terminal 4 includes a Personal Digital Assistant (PDA), a smart phone, a cellular phone, a Personal Communication Service (PCS) phone, a Global System for Mobile (GSM) phone, a Wideband CDMA (W-CDMA) phone, a CDMA-2000 phone, a Mobile Broadband System (MSB) phone, etc. which may be applied to various wired/wireless environments. In this case, the user terminal 4 may refer to a portable small-sized device, but may also be called a mobile communication terminal if it includes a camcorder, a laptop computer or the like. In an embodiment of the present invention, the user terminal 4 is not specifically limited thereto.

Furthermore, an embodiment of the present invention may include a method 2 for providing feedback information through vein authentication.

Specifically, the method 2 for providing feedback information through vein authentication includes a vein information acquisition step 22 for obtaining, by the wearable device, vein information and body composition using the photographing measurement device including the infrared radiation device and the CCD camera, the current measurement device or the current transmission device, a vein authentication step 23 for identifying a user by comparing the vein information, obtained at the vein information acquisition step, with existing vein information, a communication step 24 for sending unique bio information about the user obtained at the vein information acquisition step to the management server along with the authentication information and receiving feedback information for the transmitted information from the management server, and a storage step 25 for storing contents at the vein information acquisition step, the vein authentication step, and the communication step in a device. Furthermore, in an embodiment, the method 2 may further include a service providing step 26 for providing at least one of pieces of information about fitness equipment, sporting goods, food, and a coupon corresponding to information about the body of the user based on the results of the body composition of the user measured by the wearable device.

Furthermore, the vein authentication step 23 may include an initial input step 231 for setting the pattern of veins of the user, a vein pattern reception step 232 for receiving the pattern of veins obtained in real time when the user uses the wearable device, and an authentication step 233 for comparing the pattern of the veins obtained in real time with the pattern of the veins inputted at the initial input step and identifying the user.

Furthermore, the communication step 24 may include step 241a for receiving the vein information obtained at the vein information acquisition step (a), step 241b for receiving the authentication information obtained by the comparison and identification at the vein authentication step, and step 241c for sending, by the communication module, the obtained vein information and authentication information to the management server and receiving feedback information for the transmitted information from the management server.

Furthermore, the communication step 24 may include step 242a for storing, by the database of the management server, user information or feedback information, step 242b for receiving, by the server communication unit of the management server, the vein information and authentication information of the user obtained from the wearable device, step 242c for selecting, by the server control unit of the management server, feedback information from the database based on the received vein information and authentication information, and step 242d for sending, by the server communication unit of the management server, the feedback information selected by the server control unit to the wearable device.

Furthermore, the service providing step 26 may include step 261a for measuring a body composition or movement of the user by passing an electric current through cells within the body, step 261b for calculating a change in the body composition of the user or a change in the movement of the user, and step 261c for sending, by the communication module, information about the measured body composition or measured quantity of motion, to the management server and receiving feedback information for the transmitted information from the management server.

Alternatively, the service providing step 26 may include step 262a for storing, by the database of the management server, user information or feedback information, step 262b for receiving, by the server communication unit of the management server, information about the measured body composition or quantity of motion of the user measured by the wearable device, step 262c for selecting, by the server control unit of the management server, feedback information from the database based on the received information about the body composition or quantity of motion, and step 262d for sending, by the server communication unit of the management server, the feedback information selected by the server control unit to the wearable device.

Figure 5:
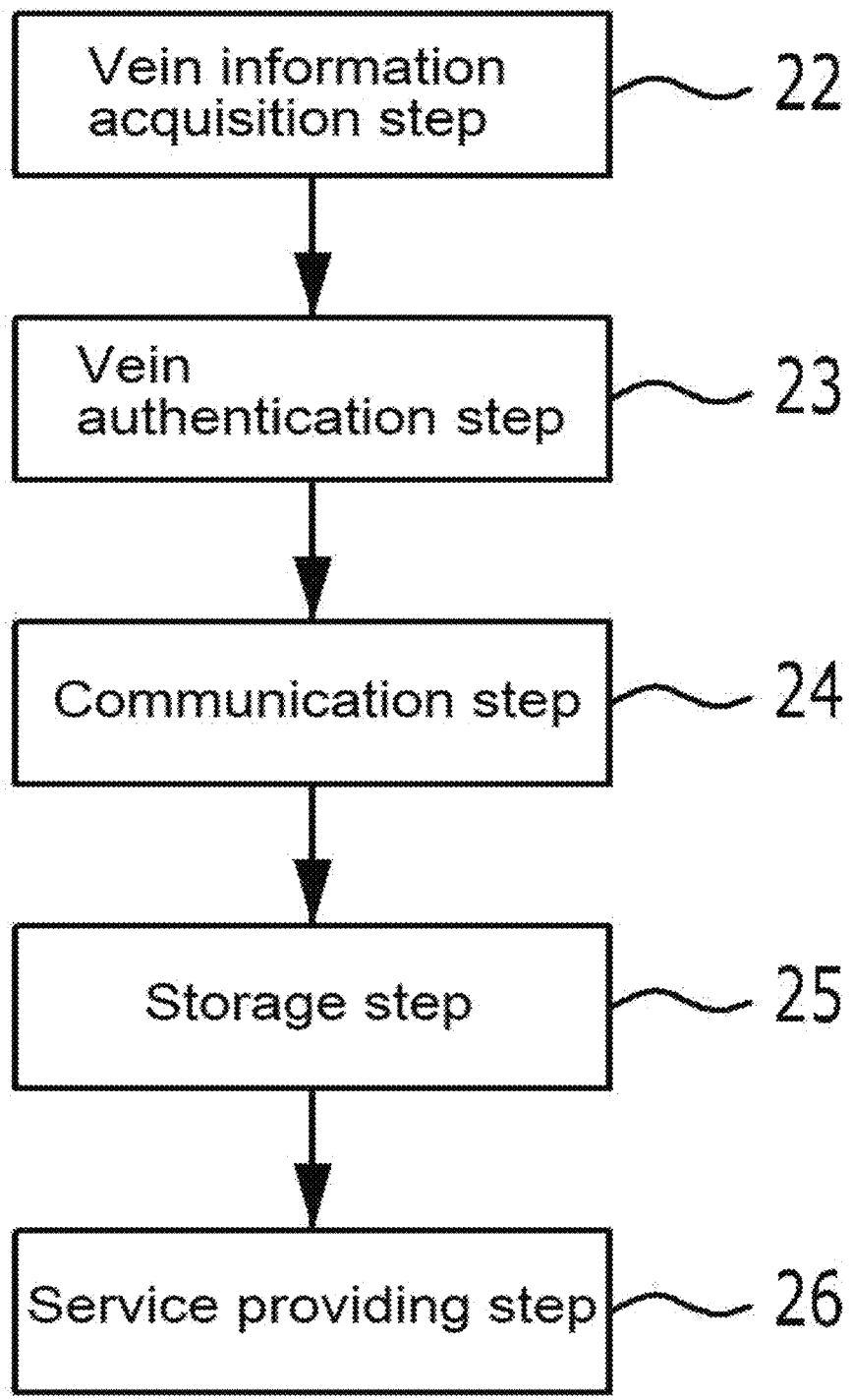
FIG. 5 is a flowchart illustrating a method for providing feedback information through vein authentication and the measurement of a body composition according to an embodiment of the present invention.

FIG. 5 is a flowchart illustrating a method for providing feedback information through vein authentication according to an embodiment of the present invention.

Figure 6:
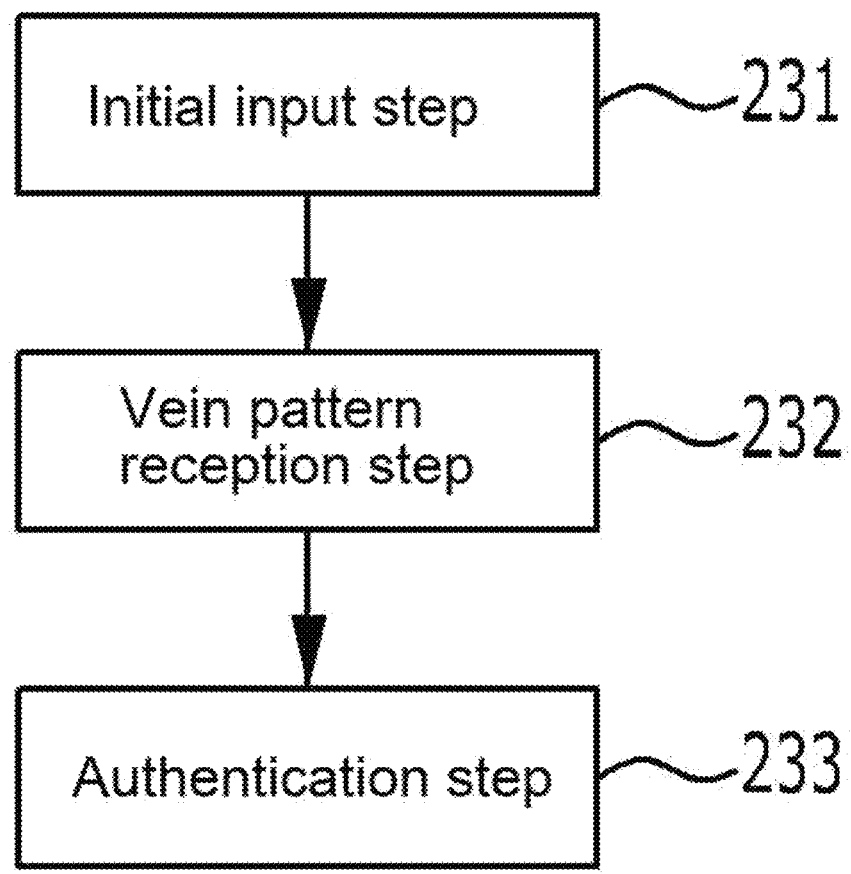
FIG. 6 is a flowchart illustrating the vein information acquisition step of the method for providing feedback information through vein authentication and the measurement of a body composition according to an embodiment of the present invention.

FIG. 6 is a flowchart illustrating the vein information acquisition step of the method for providing feedback information through vein authentication according to an embodiment of the present invention.

Referring to FIG. 5, the method for providing feedback information through vein authentication according to an embodiment of the present invention may basically include a vein information acquisition step 22, a vein authentication step 23, a communication step 24, a storage step 25, and a service providing step 26.

More specifically, the vein authentication step 23 may include an initial input step 231 for setting the pattern of veins of a user, a vein pattern reception step 232 for receiving the pattern of veins obtained in real time when the user uses the wearable device, and an authentication step 233 for comparing the pattern of the veins obtained in real time with the pattern of the veins inputted at the initial input step and identifying the user, as shown in FIG. 6.

Figure 7:
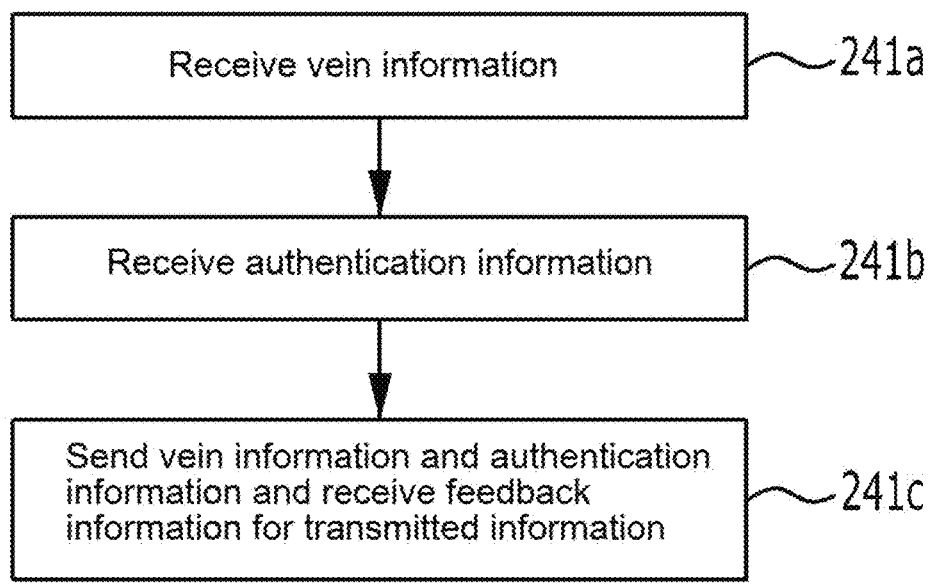
FIG. 7 is a reference diagram for illustrating the communication step of the method for providing feedback information through vein authentication and the measurement of a body composition according to an embodiment of the present invention.

FIG. 7 is a reference diagram for illustrating the communication step of the method for providing feedback information through vein authentication according to an embodiment of the present invention.

Figure 8:
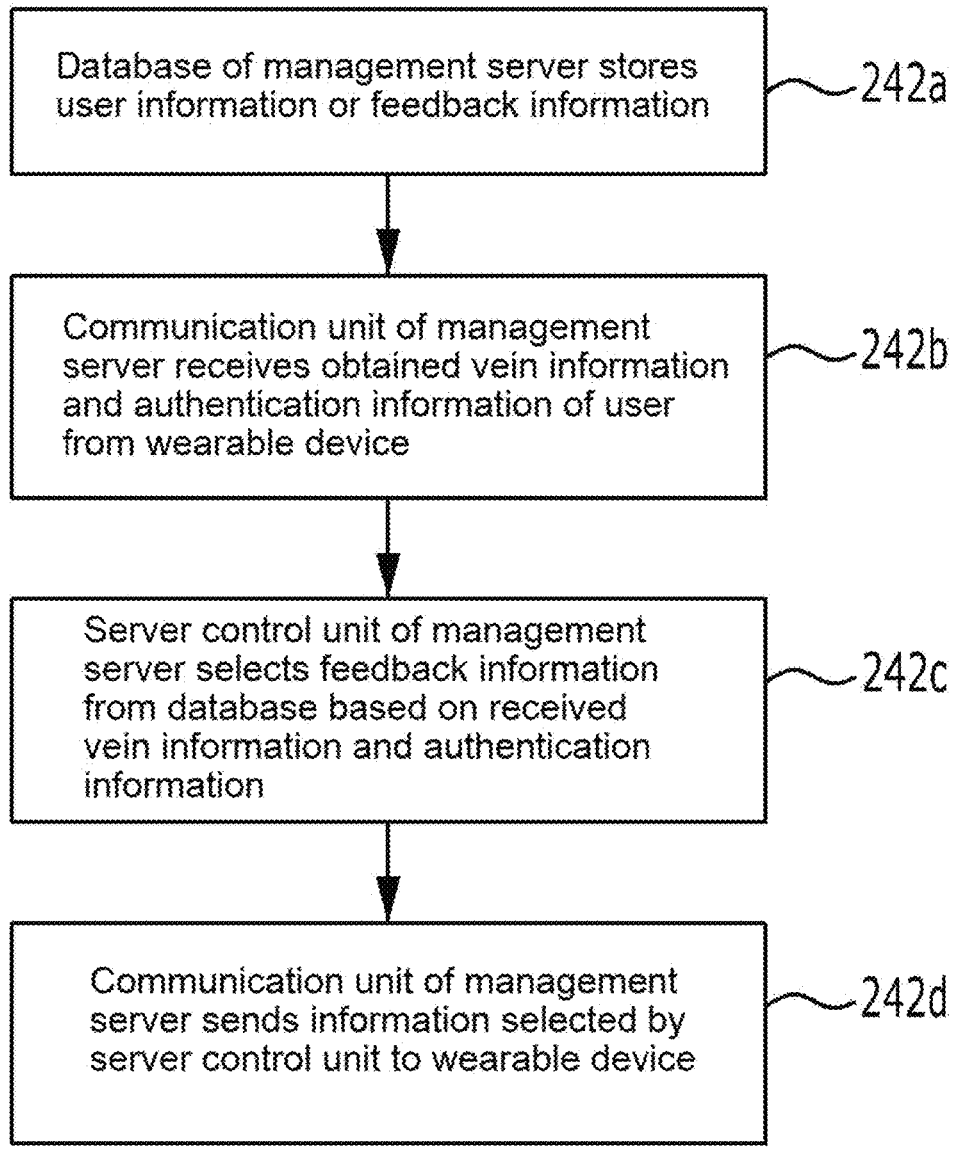
FIG. 8 is a reference diagram for illustrating the communication step of the method for providing feedback information through vein authentication and the measurement of a body composition according to an embodiment of the present invention.

FIG. 8 is a reference diagram for illustrating the communication step of the method for providing feedback information through vein authentication according to an embodiment of the present invention.

Referring to FIG. 7, the communication step 24 may include step 241a for receiving the vein information obtained at the vein information acquisition step, step 241b for receiving the authentication information obtained by the comparison and identification at the vein authentication step, and step 241c for sending, by the communication module, the obtained vein information and authentication information to the management server and receiving feedback information for the transmitted information from the management server.

Referring to FIG. 8, the communication step 24 may include step 242a for storing, by the database of the management server, user information or feedback information, step 242b for receiving, by the server communication unit of the management server, the vein information and authentication information of the user obtained from the wearable device, step 242c for selecting, by the server control unit of the management server, feedback information from the database based on the received vein information and authentication information, and step 242d for sending, by the server communication unit of the management server, the feedback information selected by the server control unit to the wearable device.

Figure 9:
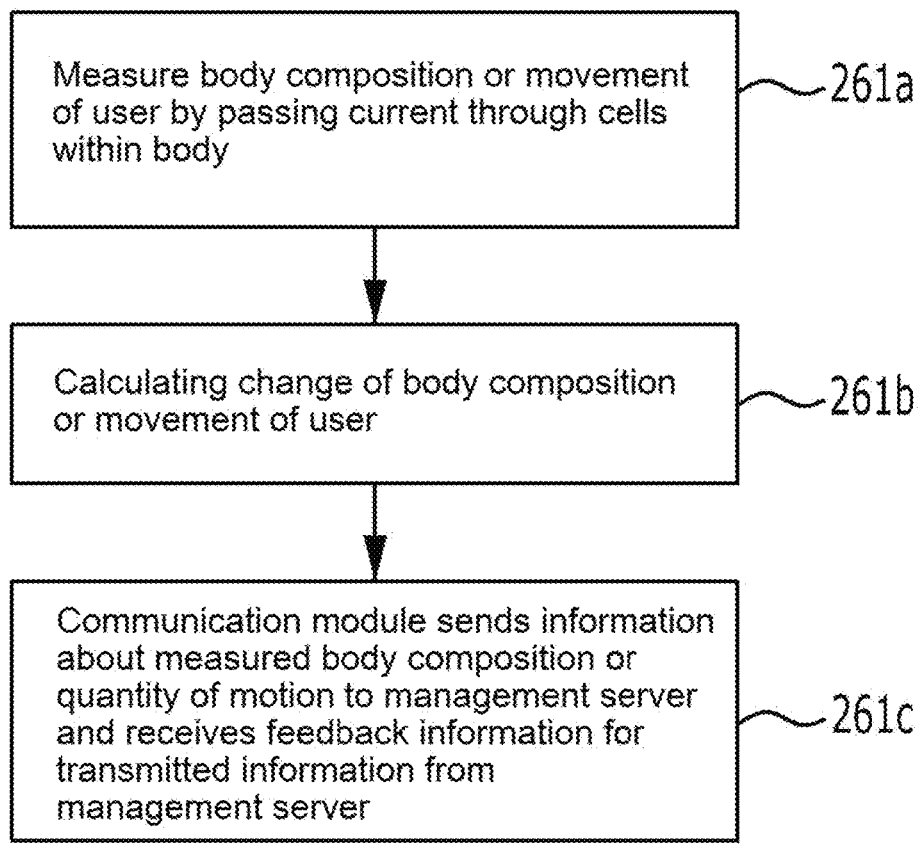
FIG. 9 is a reference diagram for illustrating the service providing step of the method for providing feedback information through vein authentication and the measurement of a body composition according to an embodiment of the present invention.

FIG. 9 is a reference diagram for illustrating the service providing step of the method for providing feedback information through vein authentication according to an embodiment of the present invention.

Figure 10:
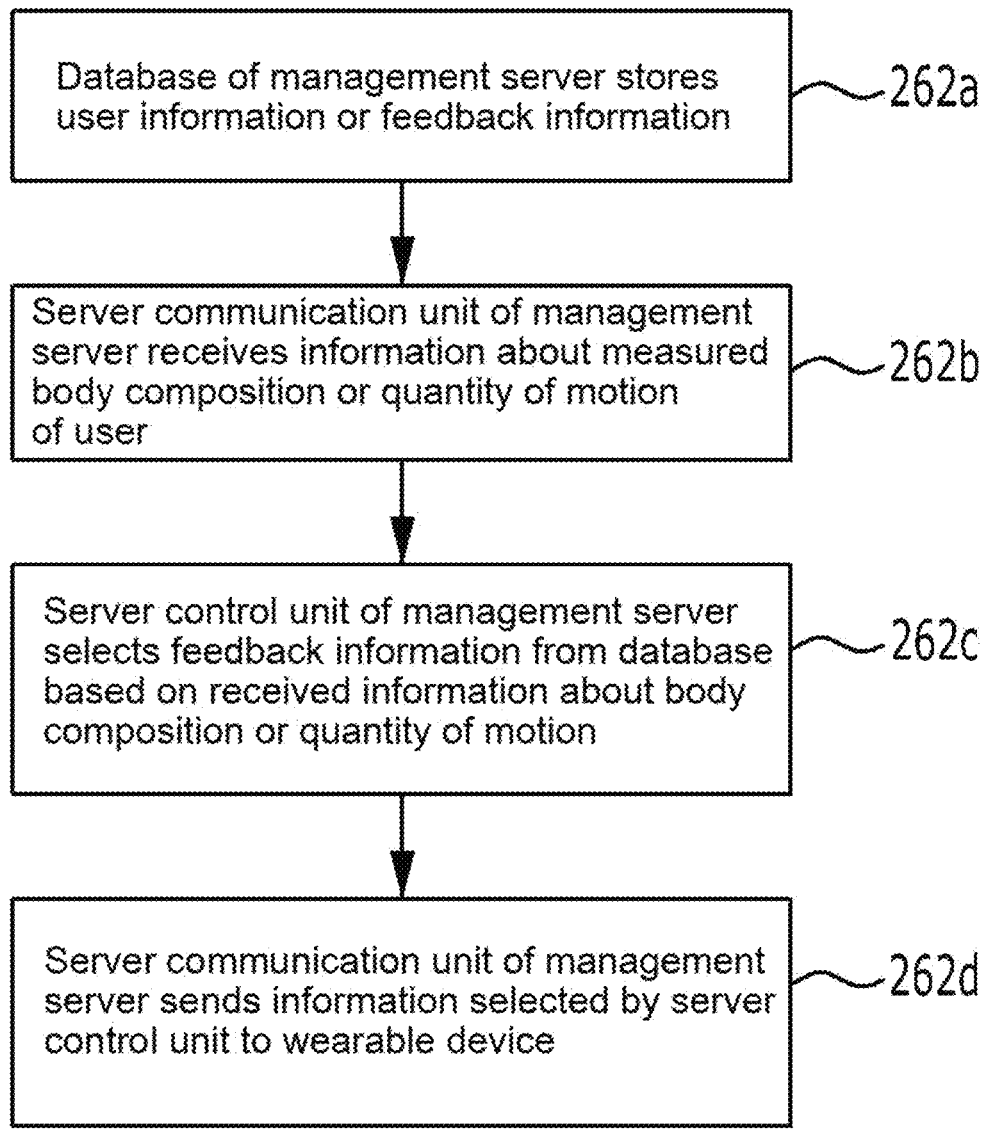
FIG. 10 is a reference diagram for illustrating the service providing step of the method for providing feedback information through vein authentication and the measurement of a body composition according to an embodiment of the present invention.

FIG. 10 is a reference diagram for illustrating the service providing step of the method for providing feedback information through vein authentication according to an embodiment of the present invention.

Referring to FIG. 9, the service providing step 26 may include step 261a for measuring a body composition or movement of the user by passing an electric current through cells within the body, step 261b for calculating a change in the body composition of the user or a change in the movement of the user, and step 261c for sending, by the communication module, information about the measured body composition or measured quantity of motion, to the management server and receiving feedback information for the transmitted information from the management server.

Referring to FIG. 10, the service providing step 26 may include step 262a for storing, by the database of the management server, user information or feedback information, step 262b for receiving, by the server communication unit of the management server, information about the measured body composition or quantity of motion of the user measured by the wearable device, step 262c for selecting, by the server control unit of the management server, feedback information from the database based on the received information about the body composition or quantity of motion, and step 262d for sending, by the server communication unit of the management server, the feedback information selected by the server control unit to the wearable device.

Figure 11:
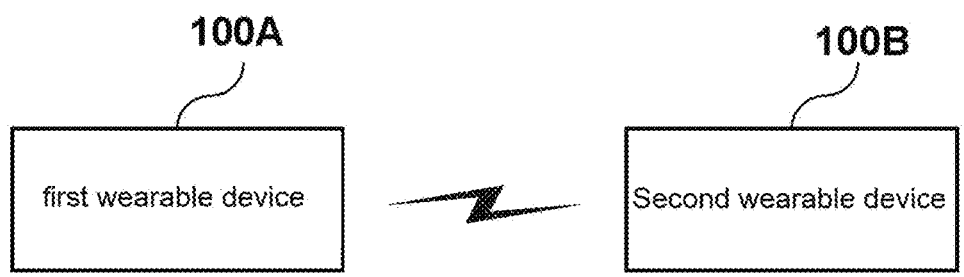
FIG. 11 is a diagram showing a payment service system using sharing payment means according to an embodiment of the present invention.

FIG. 11 is a diagram showing a payment service system using sharing payment means according to an embodiment of the present invention.

Referring to FIG. 11, the payment service system using a wearable device includes a first wearable device 100'A and a second wearable device 100'B connected through short-range communication.

When each of the first wearable device 100'A and the second wearable device 100'B detects the other party through short-range communication, it authenticates a user and sends an authentication token to the sensed wearable device if the user has been authenticated. If the authentication token received from the sensed wearable device is valid, each wearable device activates sharing payment means. In this case, the authentication token may be an authentication token that has been issued by an authentication server for issuing an authentication token and that has been stored or an authentication token generated by each wearable device.

A method for storing, by the first wearable device 100'A, information about sharing payment means and activating the sharing payment means is described below.

When the first wearable device 100'A detects the second wearable device 100'B through short-range communication, it authenticates a user. In this case, the first wearable device 100'A may authenticate the user using various types of authentication information, such as the bio information, ID/password, certificate and/or i-PIN of the user. The bio information is information by which the user can be identified, and may include a fingerprint, the iris, and a pulse rate, for example.

When the user is authenticated, the first wearable device 100'A sends a first authentication token to the sensed second wearable device 100'B. In this case, if the first authentication token is a previously stored authentication token, the first wearable device 100'A sends the previously stored authentication token to the second wearable device 100'B. Furthermore, if the first authentication token is an authentication token generated by the first wearable device 100'A, the first wearable device 100'A may generate the first authentication token by combining user ID information, an expiration date, etc. or using a random number generation algorithm, and may send the generated first authentication token to the second wearable device 100'B. In this case, the generated first authentication token may include the user ID information, the expiration date, etc. The user ID information may include information about the ID of the first wearable device. The expiration date is a valid time during which the first authentication token may be used, and may be set to 10~30 minutes, for example.

When the first wearable device 100'A performs such an operation, the second wearable device 100'B also performs the same operation as the first wearable device 100'A. In other words, when the second wearable device 100'B detects the first wearable device 100'A through short-range communication, it authenticates a user. In this case, the second wearable device 100'B may authenticate the user using various types of authentication information, such as the bio information, ID/password, certificate and/or i-PIN of the user. The bio information is information by which the user can be identified, and may include a fingerprint, the iris, and a pulse rate, for example.

When the user is authenticated, the second wearable device 100'B sends a second authentication token to the sensed first wearable device 100'A. In this case, if the second authentication token is a previously stored authentication token, the second wearable device 100'B sends the previously stored authentication token to the first wearable device 100'A. Furthermore, if the second authentication token is an authentication token generated by the second wearable device 100'B, the second wearable device 100'B may generate the second authentication token by combining user ID information, an expiration date, etc. or using a random number generation algorithm, and may send the generated second authentication token to the first wearable device 100'A. In this case, the generated second authentication token may include the user ID information, the expiration date, etc. The user ID information may include information about the ID of the second wearable device. The expiration date is a valid time during which the second authentication token may be used, and may be set to 10~30 minutes, for example.

When the first wearable device 100'A receives the second authentication token from the sensed second wearable device 100'B, it determines whether the second authentication token is valid. More specifically, the first wearable device 100'A extracts user ID information, an expiration date, etc. by analyzing the second authentication token, and determines whether the extracted user ID information is registered information and the extracted expiration date is within an expiration date. If the extracted user ID information is the registered information and the extracted expiration date is within the expiration date, the first wearable device 100'A determines that the second authentication token is valid.

If the second authentication token is valid, the first wearable device 100'A performs pairing with the second wearable device 100'B and checks sharing payment means shared with the second wearable device 100'B. Thereafter, the first wearable device 100'A determines whether the activation condition of the sharing payment means is satisfied or not, and activates the sharing payment means if the activation condition is satisfied. Accordingly, the user may perform settlement through the activated sharing payment means. In this case, the sharing payment means may include a card (e.g., a credit card or a check card) or a bankbook owned by a joint name, a membership card, a coupon and/or a payment card to be shared by members and so on. The activation condition may include an expiration date, the number of participants in the case of a meeting if the majority is members, the number of paired wearable devices and so on.

As described above, if a plurality of previously registered wearable devices is located within a predetermined distance, the first wearable device 100'A may activate sharing payment means so that settlements can be performed. Furthermore, if an activation condition in which a plurality of wearable devices registered when settlement is performed using sharing payment means should be located within a specific distance is satisfied, the first wearable device 100'A may enable settlement to be performed. In some embodiments, the first wearable device 100'A may determine that the activation condition is satisfied only when sensed wearable devices are located within a specific distance for a specific time (e.g., 10~30 minutes), and may activate the sharing payment means.

An example in which the two wearable devices are used has been described above, but the present invention may also be applied to an example in which three or more wearable devices are used.

For example, boy and girl friends may register a couple bankbook, opened at a bank, as sharing payment means, may have meals at a restaurant while wearing smart couple rings, and may then pay the meals through the sharing payment means. After the boy and girl friends are parted from each other, the boy friend tries to pay a beverage at a convenience store through the couple bankbook when he bus the beverage, but fails in the payment because settlement has not been activated.

For another example, a membership fee bankbook opened in order to save a gathering fee in an alumni association, that is, a plurality of members, may be registered as sharing payment means. When a member of the alumni association wears a corresponding wearable device and participates in a regular meeting, he or she can pay a get-together cost through the sharing payment means. After the regular meeting is finished, the director in charge of general affairs takes a taxi in order to go home and tries to pay a taxi fee through the membership fee bankbook, but fails in the payment because settlement has not been activated.

As described above, settlement is not performed only when sharing payment means is owned, but can be performed only when a co-owner of the sharing payment means satisfies a specific condition, thereby being capable of preventing the private use of public funds.

The wearable device 100' refers to a device which may be worn on a user, and may include various types, such as glasses, a watch, a bracelet, shoes, a ring, a belt, a band, a necklace, a headset, and clothing, depending on a part on which the wearable device is worn.

An application (or an applet) capable of performing payment service processing using sharing payment means may be stored in the wearable device 100'. Settlement may be performed through the sharing payment means using the application.

Such a wearable device 100' is described in detail below with reference to FIG. 12.

Figure 12:
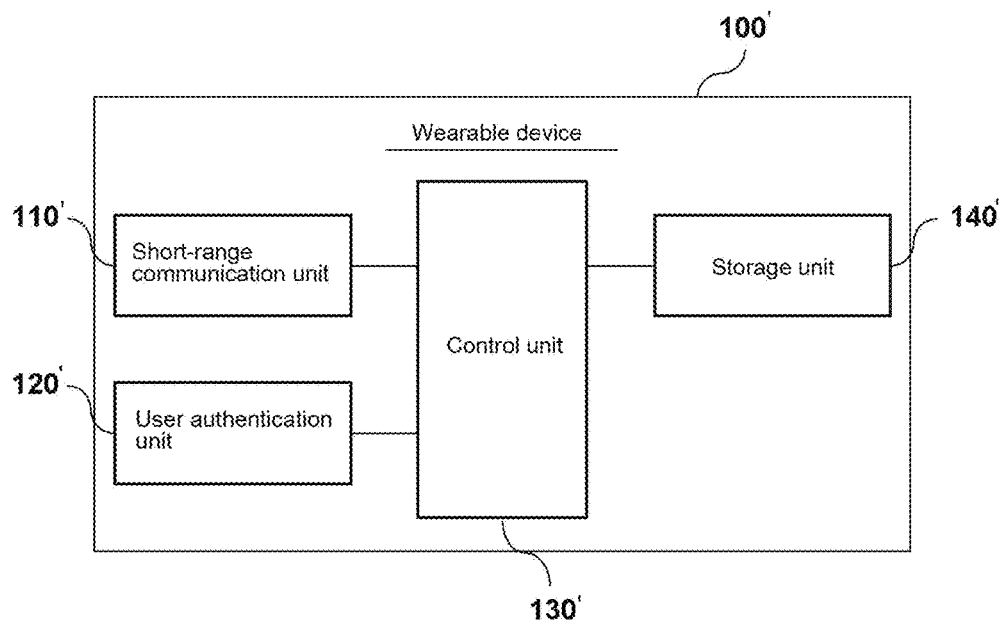
FIG. 12 is a block diagram schematically showing the configuration of the wearable device according to an embodiment of the present invention.

FIG. 12 is a block diagram schematically showing the configuration of the wearable device according to an embodiment of the present invention.

Referring to FIG. 12, the wearable device 100' includes a short-range communication unit 110', a user authentication unit 120', a control unit 130', and a storage unit 150.

The short-range communication unit 110' sends a wearable device within a short range. The short-range communication unit 110' senses a wearable device through short-range wireless communication, and may perform such sensing using various standards, such as Wi-Fi, Bluetooth communication, Zigbee communication, NFC communication, infrared rays communication (IrDA), a Radio Frequency (RF), such as a Ultra High Frequency (UHF) or a Very High Frequency (VHF), and Ultra Wideband Communication (UWB).

The user authentication unit 120' authenticates a user who has worn the wearable device 100'. The user authentication unit 120' may authenticate the user using various types of authentication information, such as bio information, an ID/password, a certificate and i-PIN. The bio information is information by which the user can be identified, and may include a fingerprint, the iris, and a pulse rate, for example.

That is, when a second wearable device is sensed through the short-range communication unit 110', the user authentication unit 120' requests the user of the second wearable device to input authentication information for user authentication. In response to the request, the user inputs the authentication information. The user authentication unit 120' compares the inputted authentication information with previously stored reference authentication information and determines that the user has been authenticated if, as a result of the comparison, the two pieces of authentication information are the same. For example, if the user is to be authenticated using bio information, the user authentication unit 120' requests input of bio information for user authentication. The user inputs the bio information, such as a fingerprint or the iris. In response thereto, the user authentication unit 120' determines whether the inputted bio information is identical with previously stored reference bio information and authenticates the user.

The control unit 130' receives sharing payment means information, including sharing payment means, information about the ID of a user who will share the sharing payment means (e.g., wearable device ID information), and the activation condition (e.g., an expiration date or the number of members) of the sharing payment means, and stores the sharing payment means information in the storage unit 140'.

Furthermore, the control unit 130' receives authentication information for user authentication and registers the received authentication information as reference authentication information.

If a user has been authenticated through the user authentication unit 120', the control unit 130' obtains a first authentication token from the storage unit 140' or generates the first authentication token, sends the generated first authentication token to a second wearable device sensed through the short-range communication unit 110', and activates sharing payment means with the second wearable device if a second authentication token received from the second wearable device is valid.

That is, if, as a result of the authentication of the user authentication unit 120', a corresponding user has been authenticated, the control unit 130' obtains the first authentication token from the storage unit 140' or generates the first authentication token and sends the first authentication token to the sensed second wearable device. In this case, if the first authentication token is identical with an authentication token stored in the storage unit 140', the control unit 130' obtains the first authentication token stored in the storage unit 140' and sends the obtained first authentication token to the second wearable device. Furthermore, if the first authentication token is identical with an authentication token generated by the wearable device 100', the control unit 130' may generate the first authentication token by combining user ID information, an expiration date, etc. or using a random number generation algorithm, and may send the generated first authentication token to the second wearable device. The first authentication token may include user ID information, an expiration date, etc. The user ID information may include information about the ID of the first wearable device. The expiration date is a valid time during which the first authentication token may be used, and may be set to 10~30 minutes, for example. The control unit 130' may generate an authentication token using conventional authentication code or various methods for generating an authentication token.

When the second authentication token is received from a sensed second wearable device, the control unit 130' may analyze the second authentication token, may extract user ID information, an expiration date, etc., and may determine whether the extracted user ID information has been stored in the storage unit 140' and whether the current time is within the extracted expiration date. If the extracted user ID information is registered information and the current time is within the extracted expiration date, the control unit 140' determines that the second authentication token is valid.

If the second authentication token is valid, the control unit 130' performs pairing with the second wearable device and extracts sharing payment means shared with the second wearable device and the activation condition of the sharing payment means from the storage unit 140' by searching the storage unit 140'. In this case, if the number of sharing payment means is plural, the control unit 130' may output the plurality of sharing payment means. The user may select at least one of the plurality of sharing payment means. Furthermore, if priority has been assigned to the plurality of sharing payment means, the control unit 130' may extract sharing payment means having the highest priority.

Thereafter, the control unit 130' determines whether the activation condition of the sharing payment means is satisfied, and activates the sharing payment means if the activation condition is satisfied. The user may perform settlement through the activated sharing payment means.

For example, the control unit 130' may determine that the activation condition is satisfied only when sensed wearable devices are located within a specific distance for a specific time (e.g., 10~30 minutes), and may activate the sharing payment means.

The control unit 130' may include at least one operation device. The operation device may be a general-purpose Central Processing Unit (CPU), a programmable device CPLD and FPGA implemented suitably for a specific purpose, an Application-Specific Integrated Circuit (ASIC) or a microcontroller chip.

The storage unit 140' functions to store data related to the operation of the wearable device 100'. In this case, known storage media may be used as the storage unit 140'. For example, one or more of known storage media, such as ROM, PROM, EPROM, EEPROM, and RAM, may be used as the storage unit 140'.

In particular, reference authentication information that enables the user authentication unit 120' to authenticate a user has been stored in the storage unit 140'. The reference authentication information is information by which a user can be authenticated (or identified), and may include bio information, an ID/password, a certificate, or i-PIN, for example.

Furthermore, the storage unit 140' stores sharing payment means information, including sharing payment means, information about the ID of a user who will share the sharing payment means (e.g., wearable device ID information), and the activation condition (e.g., an expiration date and the number of members) of the sharing payment means. In this case, the sharing payment means may include the card (e.g., credit card or check card) or bankbook of a joint name, a membership card, a coupon, and a payment card to be shared by a member and so on. The activation condition may include an expiration date, the number of participants in the case of a meeting if the majority is members.

Furthermore, the storage unit 140' may store an application (or applet) capable of performing a payment service using sharing payment means. Information stored in the storage unit 140' may be selected by the control unit 120', if necessary.

The control unit 130' may store an application (or applet) capable of performing payment service processing using sharing payment means in the storage unit 140'. Settlement can be performed using the sharing payment means by driving such an application.

The wearable device 100' according to an embodiment of the present invention may further include a display unit (not shown) for displaying various types of information related to the operation of the wearable device 100'. In particular, the display unit may display various types of information bio information measured by the user authentication unit 120', sharing payment means and so on. The display unit may be implemented using various display devices including an LCD, an LED and so on.

Furthermore, the wearable device 100' according to an embodiment of the present invention may further include an input unit (not shown) for receiving information from a user. In particular, the input unit may be used to receive information, such as sharing payment means information including sharing payment means, information about the ID of a user who will share the sharing payment means (e.g., wearable device ID information), and the activation condition (e.g., an expiration date and the number of members) of the sharing payment means, authentication information and so on. The input unit may be implemented using an input device, such as a keypad or a touch panel, a device for receiving or measuring bio information or the like. In addition, the input device may be implemented using various input devices. In some embodiments, the input unit may be implemented in the form of a touch screen integrated with the display unit.

Furthermore, the wearable device 100' according to an embodiment of the present invention may further include a power supply unit (not shown) for supplying power.

Figure 13:
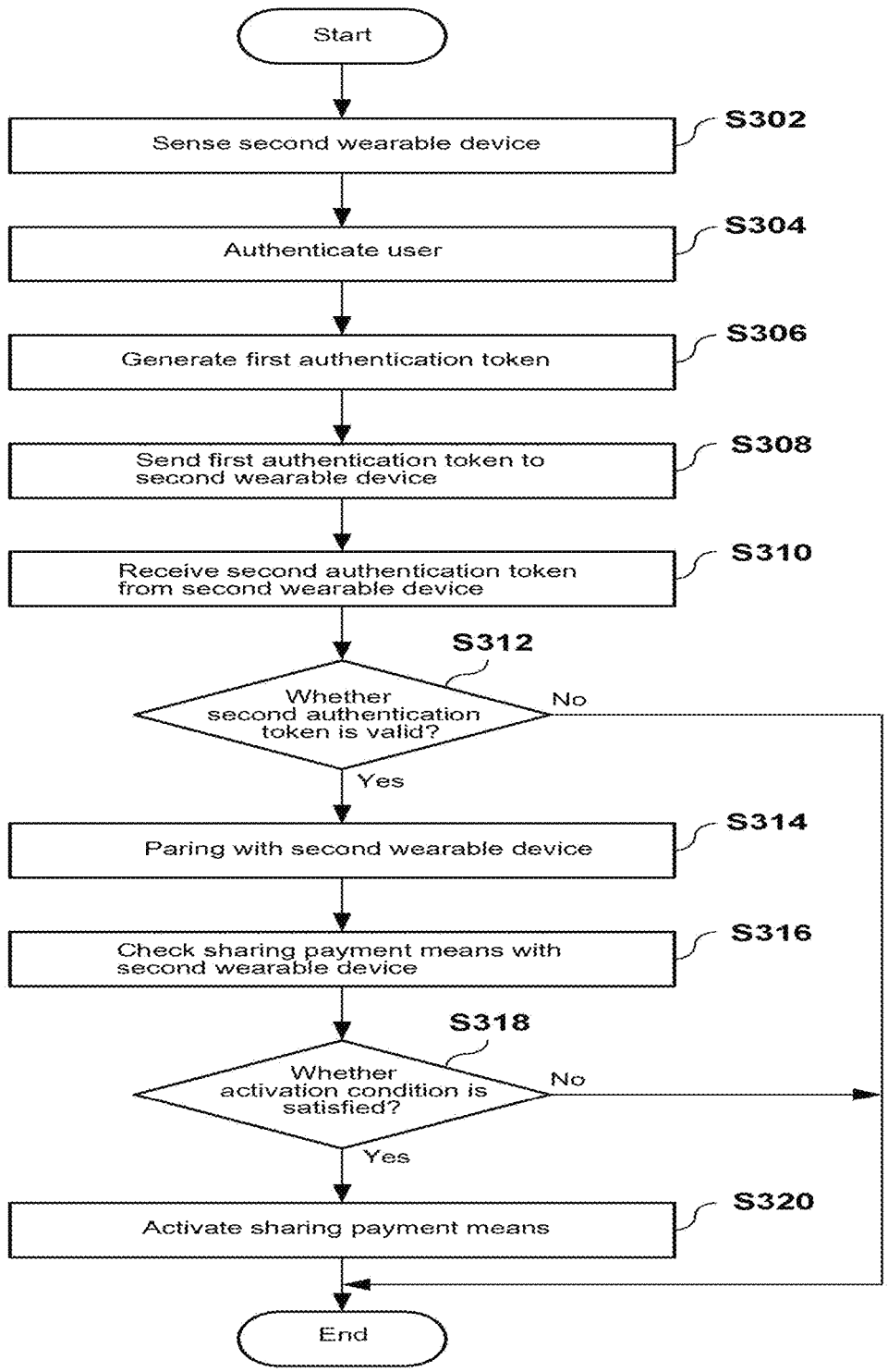
FIG. 13 is a diagram showing a method for a payment service using sharing payment means according to an embodiment of the present invention.

FIG. 13 is a diagram showing a method for a payment service using sharing payment means according to an embodiment of the present invention.

Referring to FIG. 13, when a wearable device (i.e. a second wearable device) is sensed through short-range communication at step S302, a first wearable device authenticates the user of the second wearable device at step S304. That is, when the second wearable device is sensed through short-range communication, the first wearable device obtains authentication information about the user and authenticates the user using the obtained authentication information. In this case, the first wearable device requests input of the authentication information, such as bio information, an ID/password, a certificate or i-PIN, in accordance with a predetermined authentication method. In response to the request, the user inputs the authentication information in accordance with the predetermined authentication method. The first wearable device compares the inputted authentication information with previously stored reference authentication information, and determines that the user is an authenticated user if, as a result of the comparison, the two pieces of authentication information are the same. For example, if the user is to be authenticated using bio information, the first wearable device requests the user to input bio information for user authentication. In response to the request, the user inputs the bio information, such as a fingerprint or the iris. In response thereto, the first wearable device determines whether the inputted bio information is identical with previously stored reference bio information and authenticates the user.

If, as a result of the authentication at step S304, the user is found to be an authenticated user, the first wearable device obtains or generates a first authentication token at step S306 and sends the first authentication token to the sensed second wearable device at step S308. In this case, the first authentication token may be an authentication token which has been issued by an authentication server which issues an authentication token and stored or an authentication token generated by the wearable device. The first wearable device may generate the first authentication token by combining user ID information, an expiration date, etc. or using a random number generation algorithm. The first authentication token may include user ID information, a valid time and so on. The user ID information may include information about the ID of the first wearable device.

After step S308, when a second authentication token is received from the sensed second wearable device at step S310, the first wearable device determines whether the second authentication token is valid at step S312. That is, the first wearable device analyzes the second authentication token, extracts user ID information and an expiration date from the second authentication token, and determines whether the extracted user ID information is registered information and the current time is within the extracted expiration date. If it is determined that the extracted user ID information is registered information and the current time is within the extracted expiration date, the first wearable device determines that the second authentication token is valid.

If, as a result of the determination at step S312, it is determined that the second authentication token is valid, the first wearable device performs pairing with the second wearable device at step S314, and checks sharing payment means shared with the second wearable device at step S316. In this case, if the number of sharing payment means is plural, the first wearable device outputs a plurality of sharing payment means, and the user may select at least one of the plurality of sharing payment means. Furthermore, if priority has been assigned to the plurality of sharing payment means, the first wearable device may extract sharing payment means having the highest priority.

Thereafter, the first wearable device determines whether the activation condition of the sharing payment means is satisfied at step S318. That is, the first wearable device determines whether the activation condition, such as that a predetermined number of wearable devices have been paired within the expiration date, is satisfied.

If, as a result of the determination at step S318, it is determined that the activation condition is satisfied, the first wearable device activates the corresponding sharing payment means at step S320. The user may perform settlement through the activated sharing payment means. For example, the first wearable device may determine that an activation condition is satisfied only when sensed wearable devices are located within a specific distance for a specific time (e.g., 10~30 minutes), and may activate corresponding sharing payment means.

Figure 14:
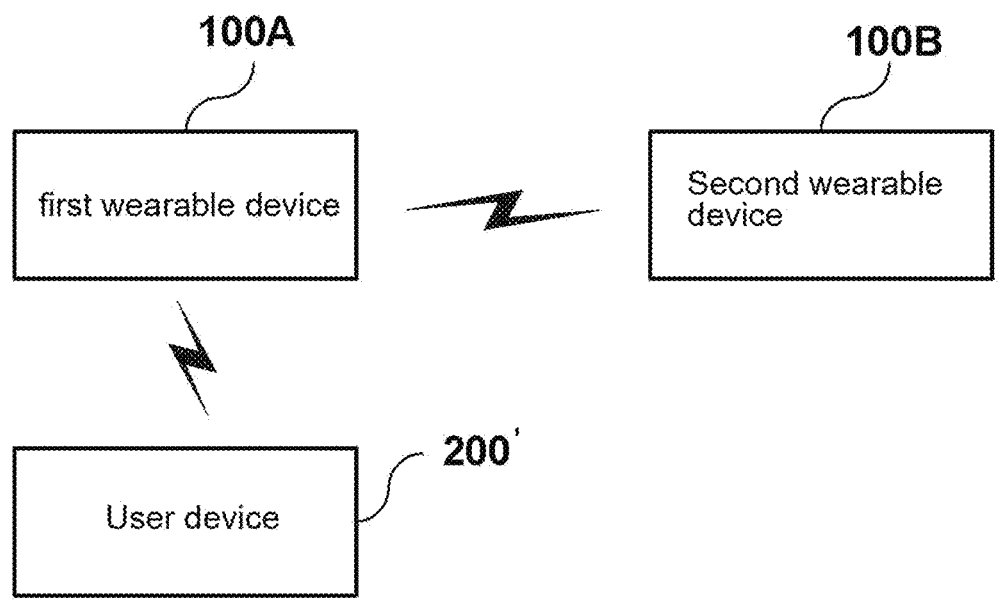
FIG. 14 is a diagram showing a payment service system using sharing payment means according to another embodiment of the present invention.

FIG. 14 is a diagram showing a payment service system using sharing payment means according to another embodiment of the present invention.

Referring to FIG. 14, the payment service system using a wearable device includes a first wearable device 100'A worn by a first user, a user device 200' in which information about sharing payment means has been stored, and a second wearable device 100'B worn by a second user, which are connected through short-range communication.

When each of the first wearable device 100'A and the second wearable device 100'B detects the other party through short-range communication, it authenticates the user of the other party. If the user is an authenticated user, each wearable device sends an authentication token to the sensed wearable device or the user device 200'. In this case, the authentication token may be an authentication token which has been issued by an authentication server which issues an authentication token and stored or an authentication token generated by the wearable device. The authentication token may include user ID information, a valid time and so on. The user ID information may include wearable device ID information and so on.

The wearable device 100' is capable of multi-pairing (e.g., pairing between wearable devices and pairing with the user device). Upon pairing between wearable devices, the wearable device 100' sends information about pairing to the user device 200', so the user device 200' can activate sharing payment means.

The user device 200' is a device paired with the first wearable device 100'A. The user device 200' receives an authentication token from the first wearable device 100'A, and activates sharing payment means if the authentication token is valid.

A method for activating sharing payment means using the user device is described below.

That is, when the second wearable device 100'B is sensed through short-range communication, the first wearable device 100'A authenticates the user of the second wearable device 100'B. In this case, the first wearable device 100'A may authenticate the user using various types of authentication information, such as the bio information, ID/password, certificate and/or i-PIN of the user. The bio information is information by which the user can be identified, and may include a fingerprint, the iris, and a pulse rate, for example.

If, as a result of the authentication, the user is an authenticated user, the first wearable device 100'A generates a first authentication token or obtains previously stored first authentication token and sends the generated or obtained first authentication token to the sensed second wearable device 100'B and the user device 200'. In this case, the first wearable device 100'A may generate the first authentication token by combining user ID information, an expiration date, etc. or using a random number generation algorithm. The first authentication token may include the user ID information, the expiration date, etc. The user ID information may include information about the ID of the first wearable device. The expiration date is a valid time for which the first authentication token may be used, and may be set to 10~30 minutes, for example.

When the first wearable device 100'A performs an operation, such as that described above, the second wearable device 100'B also performs the same operation as the first wearable device 100'A. That is, when the first wearable device 100'A is sensed through short-range communication, the second wearable device 100'B authenticates the user of the first wearable device 100'A. In this case, the second wearable device 100'B may authenticate the user using various types of authentication information, such as the bio information, ID/password, certificate and/or i-PIN of the user. The bio information is information by which the user can be identified, and may include a fingerprint, the iris, and a pulse rate, for example.

If, as a result of the authentication, the user is an authenticated user, the second wearable device 100'B generates a second authentication token or obtains previously stored second authentication token and sends the generated or obtained second authentication token to the sensed first wearable device 100'A. In this case, the second wearable device 100'B may generate the second authentication token by combining user ID information, an expiration date, etc. or using a random number generation algorithm. The second authentication token may include the user ID information, the expiration date, etc. The user ID information may include information about the ID of the second wearable device. The expiration date is a valid time for which the second authentication token may be used, and may be set to 10~30 minutes, for example.

When the second authentication token is received from the sensed second wearable device 100'B, the first wearable device 100'A sends the second authentication token to the user device 200'. That is, the first wearable device 100'A sends the first authentication token and the second authentication token to the user device 200' paired with the first wearable device 100'A.

The wearable device 100' performing such an operation has the same configuration as the wearable device 100' of FIG. 12, but is different from the wearable device 100' of FIG. 12 only in the operation of the control unit 130'. Accordingly, only the operation of the control unit 130' is described below.

The control unit 130' receives authentication information for user authentication and registers it as reference authentication information.

If the user of the sensed second wearable device 100'B is an authenticated used, the control unit 130' obtains a previously stored first authentication token or generates a new first authentication token and sends the first authentication token to the sensed second wearable device through the short-range communication unit 110'. When the second authentication token is received from the second wearable device, the control unit 130' sends the first authentication token and the second authentication token to the user device 200' paired with the wearable device 100'.

Such a wearable device 100' refers to a device which may be worn on the body of a user, and includes various types, such as glasses, a watch, a bracelet, shoes, a ring, a belt, a band, a necklace, a headset, and clothing, depending on a part on which the wearable device is worn.

When the first and the second authentication tokens are received from the first wearable device 100'A, the user device 200' determines whether the first or the second authentication token is valid. That is, the user device 200' analyzes the authentication token, extracts user ID information, an expiration date, etc. from the authentication token, and determines whether the extracted user ID information is registered information and whether the current time is within the extracted expiration date. If the extracted user ID information is registered information and the current time is within the extracted expiration date, the user device 200' determines that the authentication token is valid.

If it is determined that the first or the second authentication token is valid, the user device 200' checks sharing payment means shared with the second wearable device 100'B.

Thereafter, the user device 200' determines whether the activation condition of the sharing payment means is satisfied, and activates the sharing payment means if the activation condition is satisfied. The user may perform settlement through the activated sharing payment means. In this case, the sharing payment means may include the card (e.g., credit card or check card) or bankbook of a joint name, and a membership card, a coupon and/or a payment card to be shared by a member. The activation condition may include an expiration date, the number of participants in the case of a meeting if the majority is members and so on.

For example, the user device 200' may determine that the activation condition is satisfied only when sensed wearable devices are located within a specific distance for a specific time (e.g., 10~30 minutes), and may activate the sharing payment means.

The user device 200' includes a Personal Digital Assistant (PDA), a smart phone, a cellular phone, a Personal Communication Service (PCS) phone, a Global System for Mobile (GSM) phone, a Wideband CDMA (W-CDMA) phone, a CDMA-2000 phone, a Mobile Broadband System (MBS) phone, etc. which may be applied to various wired/wireless environments. In this case, the user device 200' may be a portable small-sized device and may refer to a mobile communication terminal if it includes a camcorder or a laptop computer. Accordingly, in an embodiment of the present invention, the user device 200' is not specifically limited to the example.

The user device 200' is described in detail with reference to FIG. 15.

As described above, settlement is not performed when a user has only to own sharing payment means, but may be performed only when a co-owner of the sharing payment means satisfies a specific condition. Accordingly, private use of public funds can be prevented.

Figure 15:
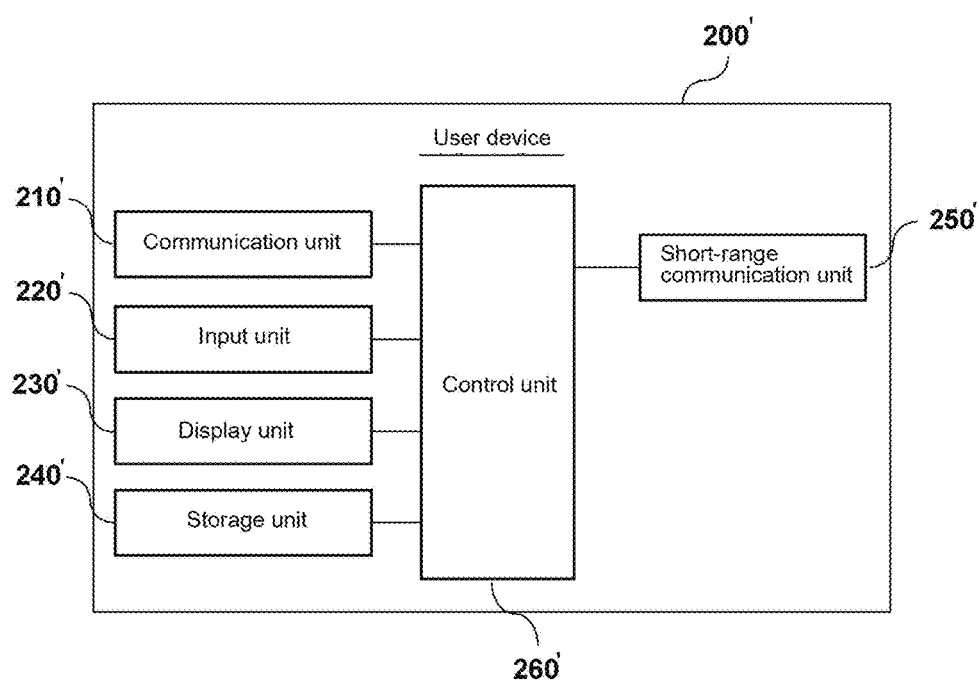
FIG. 15 is a block diagram schematically showing the configuration of a user device according to an embodiment of the present invention.

FIG. 15 is a block diagram schematically showing the configuration of the user device according to an embodiment of the present invention.

Referring to FIG. 15, the user device 200' includes a data communication unit 210' for sending and receiving data to and from various electronic devices, an input unit 220', a display unit 230', a storage unit 240', a short-range communication unit 250', and a control unit 260'.

The data communication unit 210' functions to send and receive data to and from various electronic devices. More specifically, the data communication unit 210' connects various electronic devices over a wired communication network and/or a wireless communication network. An application which provides a payment service may be downloaded using sharing payment means based on such a connection.

The data communication unit 210' may include various wired communication modules and/or wireless communication modules, and may send or receive data according to various wired and/or wireless communication standards. For example, the data communication unit 210' may be implemented in a form including various standard communication modules, such as iTU, IEEE, iSO, and iEC, and may be implemented in a form including various communication modules in addition to such standard communication modules.

The input unit 220' functions to receive information from a user. In particular, the input unit 220' may be used to receive sharing payment means information, including sharing payment means, information about the ID of a user who will share the sharing payment means (e.g., wearable device ID information), and the activation condition (e.g., an expiration date and the number of members) of the sharing payment means, and authentication information.

The input unit 220' may be implemented using a device, such as a keypad or a touch panel, and may be implemented using various input devices in addition to such an input device. Furthermore, the input unit 220' may be implemented in the form of a touch screen integrated with the display unit 230'.

The display unit 230' functions to display various types of information related to the operation of the user device 200', and may be implemented through various display devices including an LCD and an LED.

The storage unit 240' functions to store data related to the operation of the user device 200'. For example, the storage unit 240' may store various data, including data for implementing an UI, data transferred through the data communication unit 210', and data inputted through the input unit 220'. The storage unit 240' may be implemented in a form including various types of memory devices.

Furthermore, the storage unit 240' stores sharing payment means information, including sharing payment means, information about the ID of a user who will share the sharing payment means (e.g., wearable device ID information), and the activation condition (e.g., an expiration date and the number of members) of the sharing payment means. In this case, the sharing payment means may include the card (e.g., credit card or check card) or bankbook of a joint name, and a membership card, a coupon and/or a payment card to be shared by a member. The activation condition may include an expiration date, the number of participants in the case of a meeting if the majority is members and so on.

The short-range communication unit 250' may include a short-range wireless communication module, such as Wi-Fi, and communicates with the first wearable device paired with the user device 200'.

When the first and second authentication tokens are received from the first wearable device, the control unit 260' determines whether the first or the second authentication token is valid.

That is, the control unit 260' analyzes the authentication token, extracts user ID information, an expiration date, etc. from the authentication token, and determines whether the extracted user ID information is registered information and whether the current time is within the extracted expiration date. If the extracted user ID information is registered information and the current time is within the extracted expiration date, the control unit 260' determines that the authentication token is valid.

If it is determined that the first or second authentication token is valid, the control unit 260' extracts sharing payment means shared with the second wearable device and the activation condition of the sharing payment means by searches the storage unit 240'. In this case, if the number of sharing payment means is plural, the control unit 260' may output the plurality of sharing payment means, and the user may select at least one of the plurality of sharing payment means. Furthermore, if priority has been assigned to the plurality of sharing payment means, the control unit 260' may extract sharing payment means having the highest priority.

Thereafter, the control unit 260' determines whether the activation condition of the sharing payment means is satisfied, and activates the sharing payment means if the activation condition is satisfied. The user may perform settlement through the activated sharing payment means. For example, the control unit 260' may determine that the activation condition is satisfied only when sensed wearable devices are located within a specific distance for a specific time (e.g., 10~30 minutes), and may activate the sharing payment means.

Such a control unit 260' may include at least one operation device. In this case, the operation device may be a general-purpose Central Processing Unit (CPU), a programmable device CPLD and FPGA implemented suitably for a specific purpose, an Application-Specific Integrated Circuit (ASIC) or a microcontroller chip.

Figure 16:
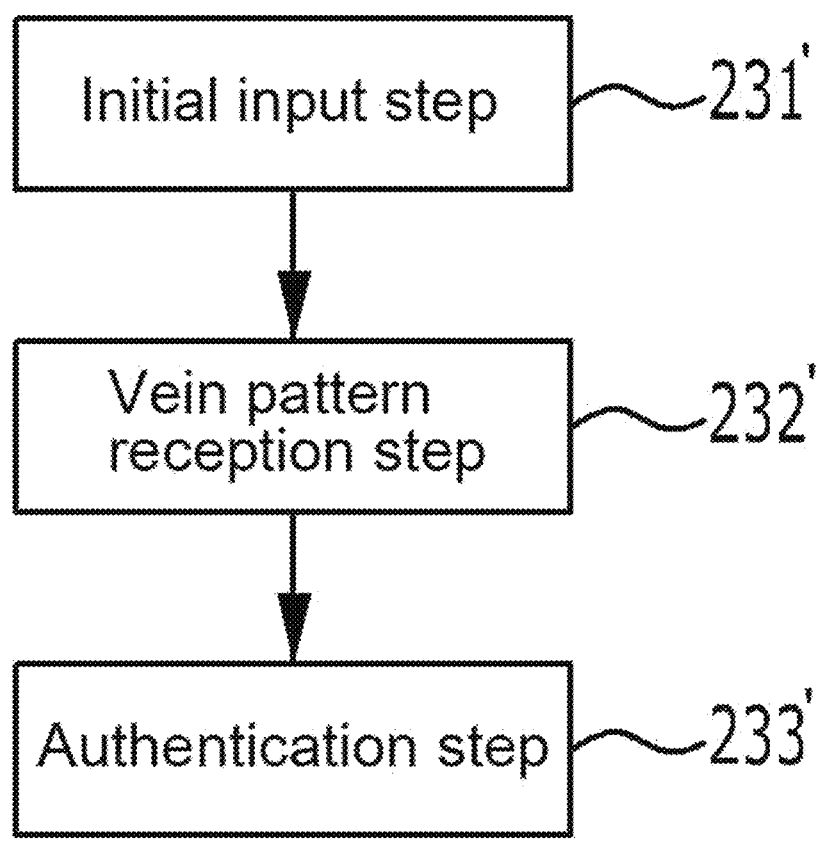
FIG. 16 is a diagram showing a payment service method using a wearable device according to another embodiment of the present invention.

FIG. 16 is a diagram showing a payment service method using a wearable device according to another embodiment of the present invention.

Referring to FIG. 16, when a wearable device (i.e., a second wearable device) is sensed through short-range communication at step S602, the first wearable device authenticates the user of the sensed wearable device at step S604. That is, when the wearable device is sensed through short-range communication, the first wearable device obtains authentication information about the user and authenticates the user using the obtained authentication information. In this case, the first wearable device requests the user to input the authentication information, such as bio information, an ID/password, a certificate, or i-PIN, in accordance with a predetermined authentication method. In response to the request, the user inputs the authentication information in accordance with the predetermined authentication method. The first wearable device compares the inputted authentication information with previously stored reference authentication information. If, as a result of the comparison, the two pieces of authentication information are the same, the first wearable device determines that the user is an authenticated user. For example, if the user is to be authenticated using bio information, the first wearable device requests the user to input the bio information for user authentication, and the user inputs the bio information, such as a fingerprint or the iris. In response thereto, the first wearable device determines whether the inputted bio information is the same as previously stored reference bio information and authenticates the user.

If, as a result of the authentication at step S604, the user is an authenticated used, the first wearable device obtains a first authentication token from the storage unit or generates the first authentication token at step S606, and sends the obtained or generated first authentication token to the sensed second wearable device at step S608. The first wearable device may generate the first authentication token by combining user ID information, an expiration date, etc. or using a random number generation algorithm. The first authentication token may include user ID information, a valid time, etc., and the user ID information may include information about the ID of the first wearable device.

After step S608 is performed, when a second authentication token is received from the sensed second wearable device at step S610, the first wearable device sends the first and the second authentication tokens to the user device paired with the first wearable device at step S612.

The user device determines whether the first or the second authentication token is valid at step S614. That is, the user device analyzes the first and the second authentication tokens, extracts the user ID information, the expiration date, etc. from each of the first and the second authentication tokens, and determines whether the extracted user ID information is registered information and whether the current time is within the extracted expiration date. If the extracted user ID information is registered information and the current time is within the extracted expiration date, the user device determines that the first and the second authentication tokens are valid.

If, as a result of the determination at step S614, it is determined that the first or the second authentication token is valid, the user device checks sharing payment means paired with the second wearable device at step S616.

The user device determines whether the activation condition of the checked sharing payment means is satisfied at step S618. That is, the user device determines whether the activation condition, such as that whether a predetermined number of wearable devices have been paired with an expiration date, is satisfied.

If, as a result of the determination at step S618, it is determined that the activation condition is satisfied, the user device activates the sharing payment means at step S620. The user may perform settlement through the activated payment means.

If, as a result of the determination at step S618, it is determined that the activation condition is not satisfied, the user device provides notification that the activation condition is not satisfied at step S622.

If, as a result of the determination at step S614, it is determined that the first or the second authentication token is not valid, the user device provides notification that the authentication token is not valid at step S624.

Figure 17:
FIG. 17 is a diagram schematically showing an apparatus for providing a user authentication service using a gait according to an embodiment of the present invention.
Figure 18:
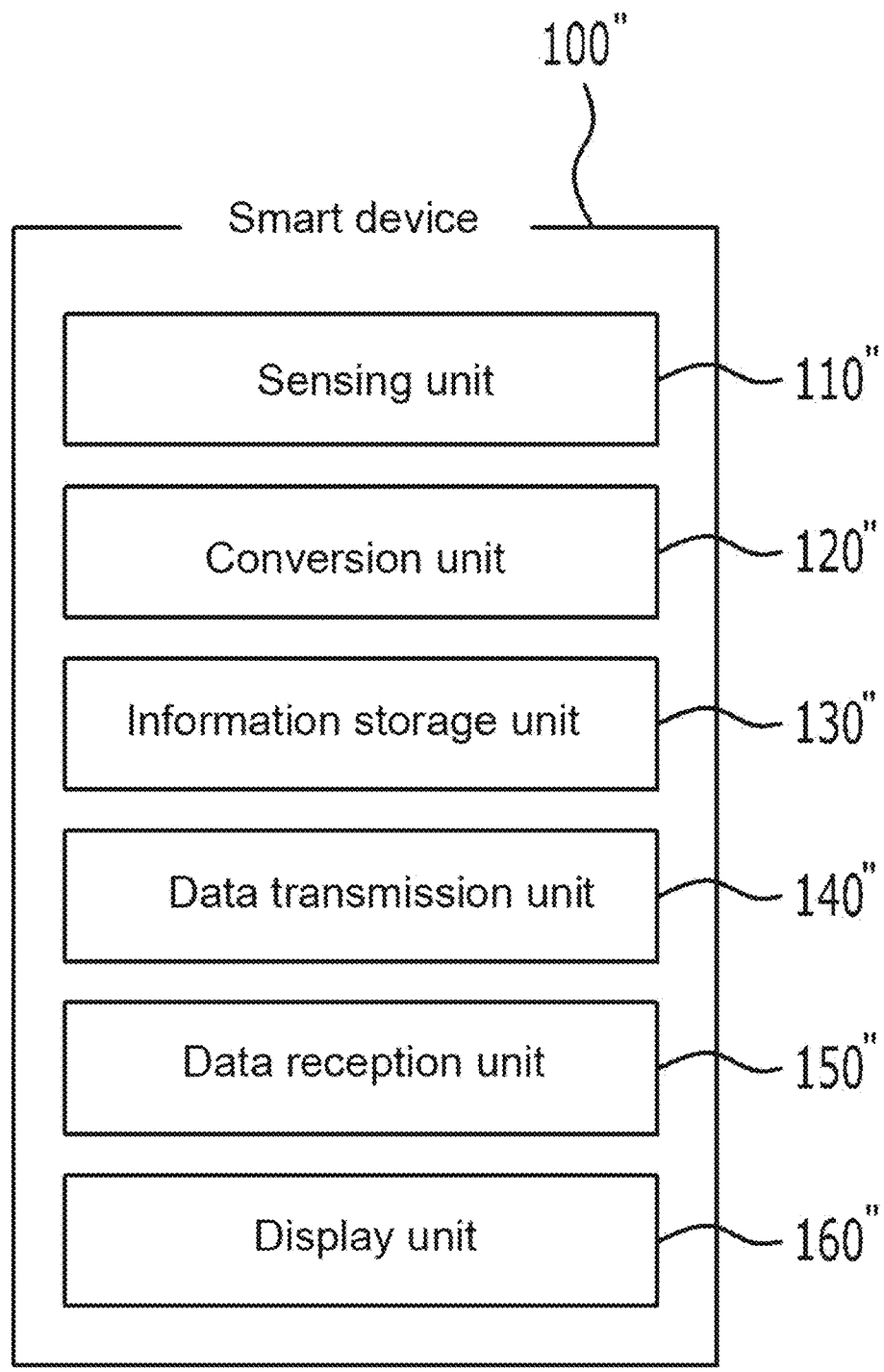
FIG. 18 is a block diagram showing the configuration of a smart device according to an embodiment of the present invention.
Figure 19:
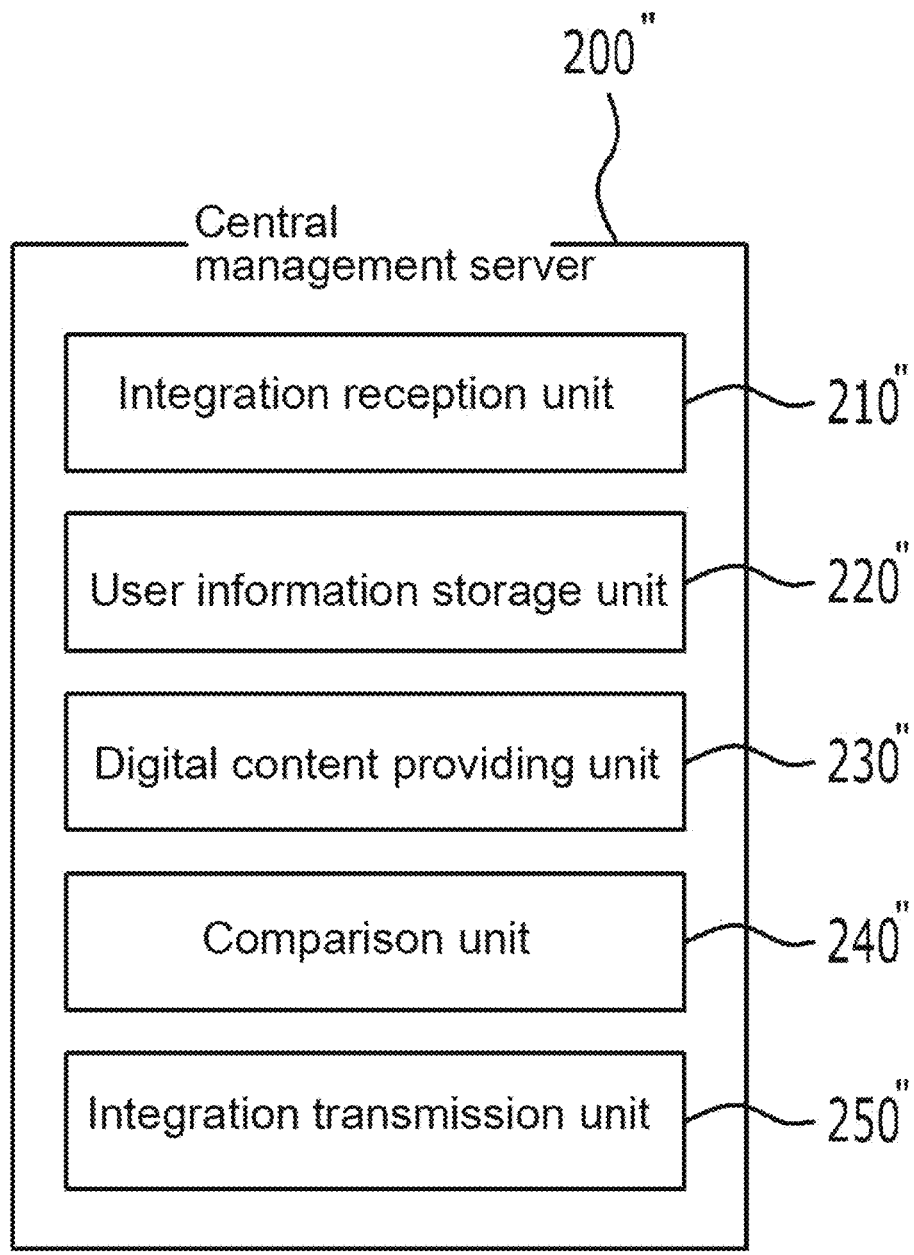
FIG. 19 is a block diagram showing the configuration of a central management server according to an embodiment of the present invention.

FIG. 17 is a diagram schematically showing an apparatus for providing a user authentication service using a gait according to an embodiment of the present invention. FIG. 18 is a block diagram showing the configuration of a smart device according to an embodiment of the present invention. FIG. 19 is a block diagram showing the configuration of a central management server according to an embodiment of the present invention.

The apparatus for providing a user authentication service according to an embodiment of the present invention refers to an apparatus for unlocking a smart device 100" or performing the login of an object that requires user authentication, such as a website, a program, or an application, or security authentication by performing the transfer of data between the smart device 100" and a central management server 200" over wired/wireless communication networks. In particular, the service providing apparatus according to an embodiment of the present invention performs user authentication using a user-specific gait.

In this case, the term "login" is a procedure for preventing others from appropriating information about the person directly concerned in a process for accessing a specific site on the Internet using the smart device 100", and may refer to a procedure for confirming a personal account in order to use services, such as the mail, blog, and bank information management of a user. In general, when a website address, i.e., an URL, is inputted to the browser of the smart device 100", a log-in screen is transmitted, and a procedure for inputting an ID and password set by a user is performed. In an embodiment of the present invention, if a user directly inputs an URL on the smart device 100", the input of an ID and password may be replaced with user authentication using gait information. Alternatively, if an app related to a service to be provided has been activated even without input of a separate URL, a series of log-in procedures including the input of an ID and password may be automatically performed through user authentication using gait information.

In this case, the security authentication may refer to common mobile phone security authentication using information between a user-unique telephone number and a communication company. In an embodiment of the present invention, upon mobile phone security authentication, when a user-unique telephone number is inputted with respect to a communication company, an authentication number is transmitted through an authentication number providing server, and the user inputs the authentication number, thereby being capable of replacing a procedure for security authentication. That is, security authentication can be performed using user bio information without the intervention of a separate authentication number providing server.

Referring to FIG. 17, the smart device 100" according to an embodiment of the present invention performs user authentication along with the central management server 200" through wired/wireless communication.

The configuration of the smart device 100" according to an embodiment of the present invention is described below.

More specifically, referring to FIG. 18, the apparatus for providing a user authentication service using a gait according to an embodiment of the present invention is a service providing apparatus based on the smart device 100". The smart device 100" may include a sensing unit 110" configured to measure the gait of a user, an information storage unit 130" configured to store the sensed gait information, a data transmission unit 140" configured to send the gait information stored in the information storage unit 130" to the central management server, a data reception unit 150" configured to receive user authentication information from the central management server, and a display unit 160" configured to display the user authentication information of the data reception unit 150" on a screen.

In this case, the smart device 100" may refer to a portable device configured to have a data communication function and to display digital content on a screen, such as a smart phone, a smart watch, or a smart band. Furthermore, the smart device 100" may correspond to one or more wearable devices which are worn or installed on a portion of the body of a person. A wearable device literally refers to a device which can be worn on the body of the human, and includes various types, such as glasses, a watch, a bracelet, shoes, a ring, a belt, a band, a necklace, a headset, and clothing, depending on a part on which the wearable device is worn. That is, the smart device 100" according to an embodiment of the present invention may correspond to a device worn on a portion of the body in addition to a handheld device shown in FIG. 20.

However, the smart device 100" is not limited to the above-described example, and includes a mobile phone, a Personal Digital Assistant (PDA), a cellular phone, a Personal Communication Service (PCS) phone, a Global System for Mobile (GSM) phone, a Wideband CDMA (W-CDMA) phone, a CDMA-2000 phone, a Mobile Broadband System (MBS) phone, a Portable Multimedia Player (PMP), a Mobile Internet Device (MID), a desktop, a tablet PC, a note book, a net book, and an information communication device which may be applied to various wired/wireless environments.

Various applications may be installed on the smart device 100". In particular, an app for recognizing a gait or a gait pattern according to an embodiment of the present invention may be installed on the smart device 100" in an application form.

A sensor installed on one side of the smart device 100" may correspond to the sensing unit 110" according to an embodiment of the present invention. Specifically, the sensing unit 110" may include any one of a terrestrial magnetic sensor for detecting location information, such as the displacement of a target object, by detecting a change or flow of a magnetic field, a gyro sensor for detecting a movement of a target object by detecting a multi-axis direction rotation speed, and an acceleration sensor for detecting the acceleration of a target object. In this case, the target object may correspond to a user himself or herself who has owned the smart device 100" or may correspond to an action sensing unit 111" to be described later. A gyro sensor or an acceleration sensor may be used as the sensing unit 110" because the distance between a target object and the sensing unit 110" may be several meters.

A gait unique to a user may be defined by recognizing all of a fine stop action, a fine acceleration, etc. using the sensing unit 110". Sensed gait information may refer to information obtained using global positioning systems (GPS) or may refer to information obtained by receiving a signal from the action sensing unit 111" attached on shoes or the body of a user for gait tracking. The sensed gait information may mean a value calculated by measuring the moving distance of a user per hour or a value calculated by measuring at least one of the stride, toe-out angle upon walking, foot angle, and walking frequency of a user. This is described later in detail.

In another embodiment of the present invention, the smart device may further include a conversion unit 120" configured to pattern a sensed gait. To this end, the conversion unit 120" may convert information unique to a gait into digital information. Furthermore, in a process for sensing the gait of a user of the smart device and digitizing the sensed gait, the conversion unit 120" may perform a procedure for encoding the sensed gait into a series of pieces of pattern information may be performed. Furthermore, if the amount of gait information is much, the conversion unit 120" may perform a procedure for compressing the gait information. As will be described later, information about a user-specific gait, which has been encoded into pattern information, may be the subject to be compared with user information which has been previously stored in the central management server. A method for patterning a gait may include a method for measuring and collecting a walking time, a stride, and a toe-out angle, a foot angle, and a walking frequency upon walking and converting them into digital data.

The information storage unit 130" may store gait information about the gait of the user. In this case, the gait information may be subdivided into real-time gait information, unique information, and related data for the user. The real-time gait information may refer to data currently recognized by the smart device 100". The unique information may refer to data that belongs to real-time gait information and that is recognized as the gait of a specific user. The related data may refer to additional data, such as noise filtered from the real-time gait information and unique information of a user.

The unique information may be registered with user information stored in the user information storage unit 220" of the central management server 200", and may be the subject to be compared with gait information received by the central management server 200".

The information storage unit 130" may collect data before sending gait information to the central management server 200" and may manage real-time gait information, unique information, and related data. Furthermore, the information storage unit 130" may play the role of a filter for storing only real-time gait information and unique information other than additional data.

More specifically, the information storage unit 130" functions to store data, includes a main memory device and an auxiliary memory device, and may store application programs necessary for the functional operation of the smart device 100". The information storage unit 130" may basically include a program region and a data region. In this case, when each function is activated in response to a request from a user, the smart device 100" provides each function by executing a corresponding application program under the control of a control unit (not shown).

In particular, the information storage unit 130" according to an embodiment of the present invention may store an operating system for booting the smart device 100", a program for providing services including a user authentication service, an application program for providing a user authentication service and so on. The data region is a region in which user cookies generated when the smart device 100" is used are stored. In this case, the data region may refer to a region in which cookies about gait information are stored. Furthermore, the expiration date of gait information may be set depending on interlocking between the smart device 100" and the central management server 200".

The data transmission unit 140" is included in the smart device 100" and functions to transfer gait information, stored in the information storage unit 130", to the central management server 200". The data reception unit 150" functions to receive user authentication information that is returned from the central management server 200" to the smart device 100".

More specifically, the data transmission unit 140" and the data reception unit 150" sends and receives data for the exchange of user authentication information between the smart device 100" and the central management server 200". The data transmission unit 140" and the data reception unit 150" may include RF transmission means for up-converting and amplifying the frequency of a transmitted signal, RF reception means for low-noise amplifying a received signal and down-converting the frequency of the signal and so on.

The data transmission unit 140" and the data reception unit 150" may include at least one of a wireless communication module (not shown) and a wired communication module (not shown). Furthermore, the wireless communication module may include at least one of a wireless network communication module, a Wireless Local Area Network (WLAN) (or Wireless Fidelity (Wi-Fi) or Worldwide Interoperability for Microwave Access (WiMAX) communication module, and a Wireless Personal Area Network (WPAN) communication module. The wireless communication module functions to send and receive data according to a wireless communication method. If the smart device 100" uses wireless communication, it may send data to or receive data from the central management server 200" using any one of the wireless network communication module, the WLAN communication module, and the WPAN communication module.

The wireless network communication module functions to access a communication network through a base station and to send and receive data. When gait information is stored in the information storage unit 130", the wireless network communication module may access a communication network through a base station and send data to the central management server 200". Furthermore, the wireless network communication module may access a communication network through a base station, may receive user authentication information from the central management server 200", and may provide received gait information to the display unit 160".

The display unit 160" functions to visualize data so that user authentication information, that is, whether authentication has been completed or whether authentication has failed, can be checked. More specifically, the display unit 160" displays information about a series of pieces of operating state, operating results, etc. which are generated while a function of the smart device 100" is performed. Furthermore, the display unit 160" may display the menus of the smart device 100".

In this case, the display unit 160" may include a Liquid Crystal Display (LCD), a Thin Film Transistor LCD (TFT-LCD), Organic Light Emitting Diodes (OLED), a Light-Emitting Diode (LED), an Active Matrix Organic LED (AMOLED), a flexible display, a 3-dimensional (3D) display, etc. In this case, the display unit 160" may be formed in a touch screen form. If the display unit 160" is formed in a touch screen form as described above, it may perform all or some of the functions of input means. In particular, the display unit 160" according to an embodiment of the present invention displays user authentication information received from the central management server 200".

Referring back to FIG. 17, the apparatus for providing a user authentication service using a gait according to an embodiment of the present invention may perform a user authentication service by associating the smart device 100" and the central management server 200" over a wired/wireless communication network.

In this case, the wired/wireless communication network includes a base station controller, a base station transmitter and/or a relay station. The base station controller functions to relay a signal between the base station transmitter and a switching station. The wired/wireless communication network supports both a synchronous method and an asynchronous method. Accordingly, in the case of the synchronous method, a Base Station Transmission System (BTS) may be a transmission/reception base station transmitter and a Base Station Controller (BSC) may be a transmission/reception base station controller. In the case of the asynchronous method, a Radio Transceiver Subsystem (RTS) may be a transmission and reception base station transmitter, and a Radio Network Controller (RNC) may be a transmission and reception base station controller. The wired/wireless communication network according to an embodiment of the present invention is not limited thereto, and may collectively refer to a GSM network other than a CDMA network and networks which may be used in the access network of a next-generation mobile communication system to be developed in the future.

The wired/wireless communication network may further include an access point. The access point is a small base station, such as a femto or pico base station chiefly disposed in a building. The femto or pico base station is classified depending on how many the smart devices 100" can be accessed in terms of the classification of a small base station. Furthermore, the access point includes a short-range communication module for performing short-range communication, such as Wi-Fi, with the smart device 100". The short-range communication may be performed in accordance with various standards, such as Bluetooth communication, beacon communication, Zigbee communication, infrared rays communication (IrDA), a Radio Frequency (RF) including a Ultra High Frequency (UHF) and a Very High Frequency (VHF), and ultra-wideband communication (UWB), in addition to Wi-Fi. The access point may extract the location of a data packet, may designate the best communication route for the extracted location, and may transfer the data packet to a next device, for example, the smart device 100" along the designated communication route. The access point may be shared by several lines in a common network environment.

The access point is basically divided into a fixed type access point and a mobile type access point. The fixed type access point may include a router, a repeater, a relay station, etc. The mobile type access point may include the bridge product of a specific manufacturer, such as KT's Egg. Such a mobile type access point may read a reception-side address from transmission-side information while guaranteeing free mobility, may designate the most appropriate communication route, and may send data.

As shown in FIG. 19, the central management server 200" according to an embodiment of the present invention may include an integration reception unit 210" configured to receive data from the data transmission unit 140", a comparison unit 240" configured to compare data, received from the data transmission unit 140", with previously stored user information, and an integration transmission unit 250" configured to send user authentication information to the data reception unit 150".

The integration reception unit 210" and the integration transmission unit 250" may be responsible for receiving gait information from a plurality of users and various smart devices 100" and for sending the gait information to the smart devices 100" of the users. The integration reception unit 210" and the integration transmission unit 250" may include a plurality of signal channels so that mass data is received and transmitted. In this case, the term "integration" may mean that data used or communicated by a plurality of users is collected and managed in a single form.

In accordance with an embodiment of the present invention, the central management server 200" may further include a user information storage unit 220" configured to previously store information about a user. User information stored for user authentication may have been previously stored using the sensing unit 110" before a service according to an embodiment of the present invention is used. Regarding the user information, the most reliable information may be stored by correcting an error when pieces of gait information are collected. In this case, the user information may refer to subscription information for a characteristic website, finance, administrative organ, etc. including user-specific gait information, that is, specific information, such as the name, address, ID and/or password of a user.

The comparison unit 240" according to an embodiment of the present invention compares gait information, received through the integration reception unit 210", with previously stored user information and determines whether user authentication is a success or a failure.

A decoding function may be installed on the comparison unit 240" because gait information may be patterned and transferred. In some embodiments, if user information itself stored in the user information storage unit 240" has been patterned and stored, patterned gait information may be used for an analysis and comparison without any change.

The comparison unit 240" may compare previously stored information with information received from a single smart device 100" at the same time or at once in a one-to-one or one-to-many manner.

In another embodiment of the present invention, the apparatus for providing a user authentication service using a gait may further include a digital content providing unit 230". The authentication of a user is performed by comparing gait information received from the central management server 200" with previously stored user information. If, as a result of the authentication, the user is found to be an authenticated user, the digital content providing unit 230" may send digital content to the user.

In the digital content, "digital" refers to an information representation method, and "content" collectively refers to information, knowledge, and a database having various forms, such as a symbol, a character, a sound, video, a picture and/or an image. The digital content corresponds to the contents having a form, such as a character, a sound, a picture or an image distributed through the Internet, and does not refer to only information and simple contents, but refers to content having transaction and services inherent therein as assets that create added values using several information technologies.

For example, the digital content may include an application that is transferred to the smart device 100" and executed and that is related to a service provided by a service providing company (or an affiliated company), an electronic coupon related to an affiliated store, an electronic coupon related to a membership and so on. Alternatively, the digital content may also correspond to content which is provided by a website or finance-related application that a user attempts to access in an event form.

The digital content providing unit 230" is an additional element, and may directly provide a user with digital content for a login and security authentication process without user authentication through the comparison unit 240".

As an example in which digital content is provided, when a user performs user authentication using a gait based on the smart device 100", if the user is determined to be a legitimately authenticated user in association with the central management server 200", a website or finance-related application that the user attempts to access may automatically send an electronic coupon to the user. In addition, a customized service may be provided to an authenticated user. Such a customized service is based on previously obtained information about the user.

A method for recognizing the gait of a user using the smart device 100" according to an embodiment of the present invention is described below with reference to FIGS. 20 to 24.

Figure 20:
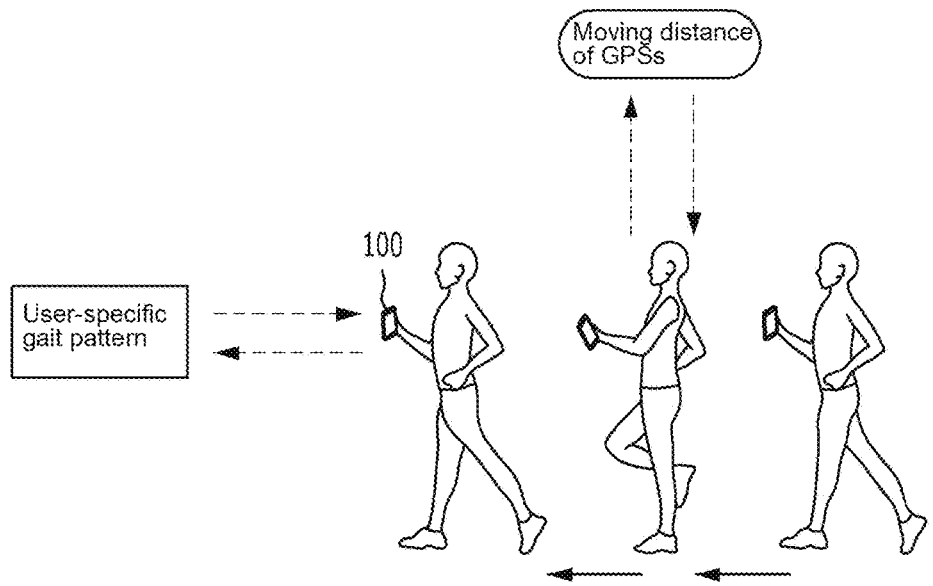
FIG. 20 is a diagram showing the state in which gait information is collected using a smart device according to an embodiment of the present invention.
Figure 21:
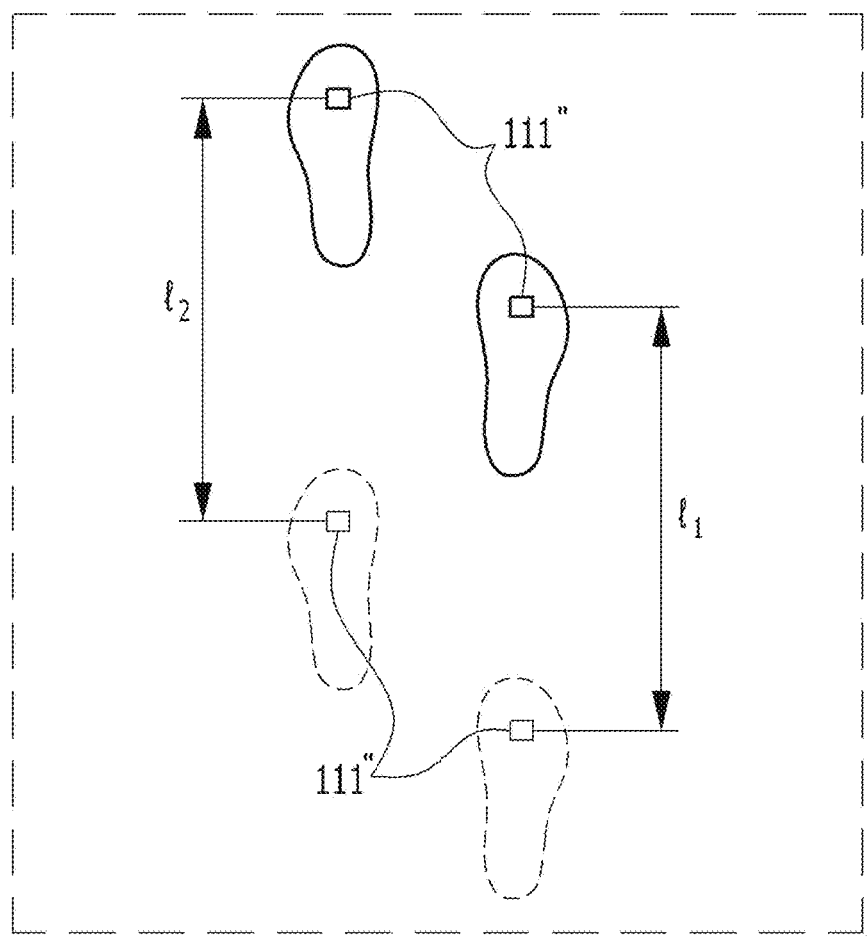
FIG. 21 is a diagram illustrating a method for collecting gait information based on a stride according to an embodiment of the present invention.
Figure 22:
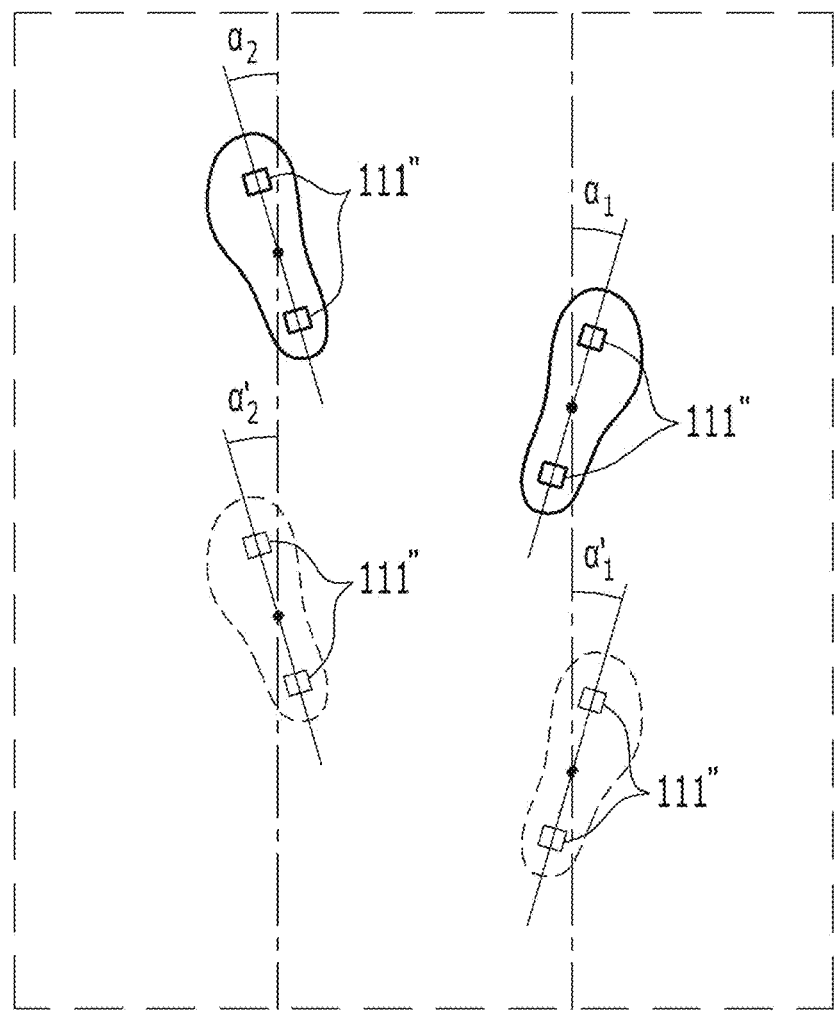
FIG. 22 is a diagram illustrating a method for collecting gait information based a toe-out angle according to an embodiment of the present invention.
Figure 23:
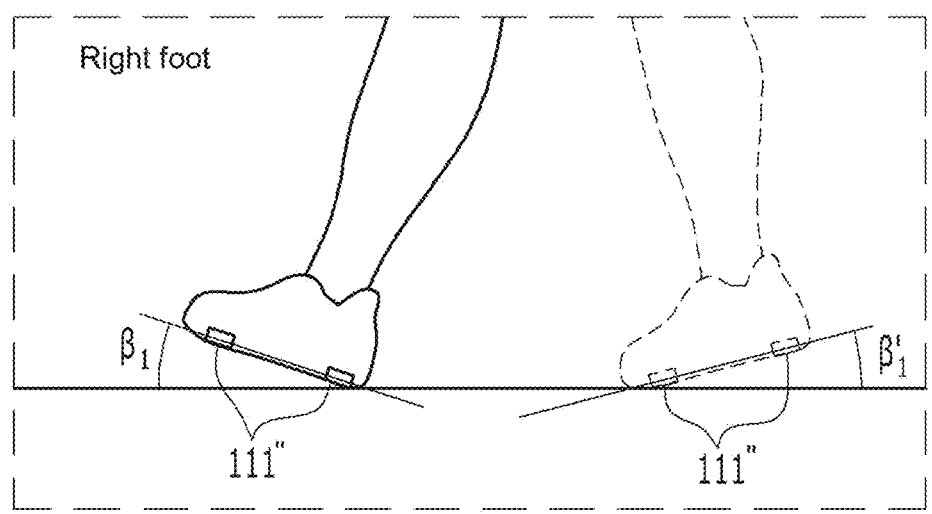
FIG. 23 is a diagram illustrating a method for collecting gait information based on a foot angle according to an embodiment of the present invention.
Figure 24:
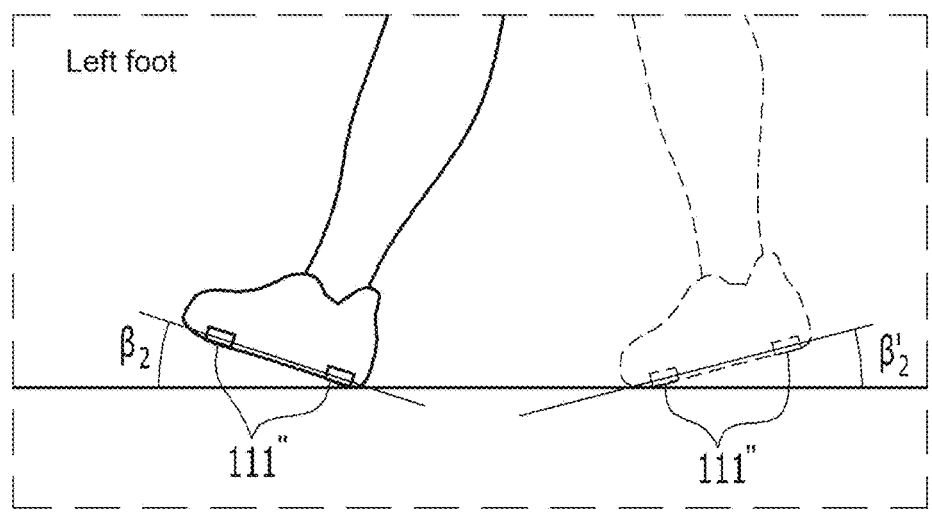
FIG. 24 is a diagram illustrating a method for collecting gait information based on a foot angle according to an embodiment of the present invention.

FIG. 20 is a diagram showing the state in which gait information is collected using the smart device according to an embodiment of the present invention. FIG. 21 is a diagram illustrating a method for collecting gait information based on a stride according to an embodiment of the present invention. FIG. 22 is a diagram illustrating a method for collecting gait information based a toe-out angle according to an embodiment of the present invention. FIG. 23 is a diagram illustrating a method for collecting gait information based on a foot angle according to an embodiment, which is different from the embodiment of FIG. 22. FIG. 24 is a diagram illustrating a method for collecting gait information based on a foot angle, which is different from the embodiment of FIG. 22.

Referring to FIG. 20, the smart device 100" recognizes unique gait information according to a movement of a user so that user authentication is performed. The gait information may be converted into patterned information as described above.

The gait information is recognized using the sensing unit 110", but a detailed execution method thereof may be performed according to the following various embodiments.

As shown in FIG. 20, gait information may be indirectly recognized in association with Global Positioning Systems (GPS) or may be obtained by receiving signals from the action sensing unit 111" that is directly attached to the shoes or body of a user for gait tracking.

Specifically, if gait information is obtained using GPSs, it may be obtained by measuring the moving distance of a user per hour and dataficating a value calculated using the measured moving distance or may be obtained by dataficating a route along which a user has moved from one place to the other place.

By way of example, a route along which a user has normally moved may be divided into short partitions for each section and stored. A pattern related to the gait of the user may be extracted by measuring a moving distance per hour.

More specifically, a method for obtaining a signal from the action sensing unit 111" may be performed using at least one of the stride, and toe-out angle, foot angle, and walking frequency upon walking. That is, only one piece of information of the stride, and toe-out angle, foot angle, and walking frequency upon walking may be obtained from the action sensing unit 111" or two or more pieces of information of them may be obtained and used as gait information. In this case, the action sensing unit 111" is attached to any one foot or feet of a user in order to obtain the gait information, and the size, shape, and additional function of the action sensing unit are not limited. Any device or unit capable of sending specific data, such as gait information, to the smart device 110" may be used as the action sensing unit 111".

If the action sensing unit 111" is attached to shoes, it may have a form, such as an electronic tag. If the action sensing unit 111" is attached to the body, it may correspond to a wearable device which may be worn on the ankle or the inside of a thigh. Specifically, the action sensing unit 111" may have a form, such as a band or a bracelet, and may have a form of an electronic tag formed to be attached to pants.

Accordingly, in the drawings according to embodiments of the present invention, the action sensing unit 111" has been illustrated as having a tag form attached to shoes, for convenience of description, but it is to be noted that the action sensing unit 111" is not necessarily limited to such a form.

Furthermore, the action sensing unit 111" and the sensing unit 110" of the smart device 100" according to an embodiment of the present of invention may exchange gait information using a short-range wireless communication method. The short-range communication method includes various short-range communication standards, such as Bluetooth communication, beacon communication, Zigbee communication, infrared rays communication (IrDA), a Radio Frequency (RF), such as a Ultra High Frequency (UHF) and a Very High Frequency (VHF), and Ultra Wideband Communication (UWB), in addition to Wireless Fidelity (Wi-Fi).

The action sensing unit 111" may be attached to both shoes or feet of a user. At least one action sensing unit 111" may be attached to a shoe on one side or a foot. The action sensing unit 111" may be located at any of the front, middle, and back of the center of the foot. If the action sensing unit 111" is directly attached to a foot of a user other than a shoe, it may be located at any one place, such as the sole of the foot, the top side of the foot, the ankle, or the inside of a thigh, or may be located at a plurality of the places in order to obtain gait information. However, the action sensing unit 111" may be attached to a shoe in terms of economic feasibility or user convenience.

FIG. 21 shows the state in which a user has taken steps forward one by one in the state in which the action sensing unit 111" has been attached to the front of each foot of the user. A stride is different for each user. In general, the stride of a left foot and the stride of a right foot are different. The moving distance 11 of a right foot and the moving distance 12 of a left foot are measured based on such a characteristic and then converted into data.

FIG. 22 shows the state in which a user has taken steps forward one by one in the state in which the action sensing units 111" have been attached to the front and back of the feet. A toe-out angle upon walking is different for each user. In general, the toe-out angle of a left foot and the toe-out angle of a right foot are different. The toe-out angle $\alpha1$ of the right foot and the toe-out angle $\alpha2$ of the left foot are measured based on such a characteristic and then converted into data. In an alternative embodiment, a change "$\alpha1'\text{->}\alpha1$" of the toe-out angle of the right foot and a change "$\alpha2'\text{->}\alpha2$" of the toe-out angle of the left foot may be measured and then converted into data. In some embodiments, a change "$\alpha1'\text{->}\alpha1$" of the toe-out angle of the right foot and a change "$\alpha2'\text{->}\alpha2$" of the toe-out angle of the left foot may be measured, and an average value of the changes may be calculated and then converted into data.

In this case, the toe-out angle $\alpha1$ or $\alpha2$ may be measured based on a virtual line that connects the center points of the front and back action sensing units 111" when a user takes a step forward.

FIGS. 23 and 24 show the state in which a user has taken a step forward by moving a right foot and a left foot in the state in which the action sensing units 111" have been attached to the front and back of the feet. By noticing that each user has a different foot angle, user-specific gait information may be obtained by measuring an angle $\beta'1$ formed by the surface of the earth and the ball of a right foot and an angle $\beta1$ formed by the surface of the earth and the kick heel of the right foot. The same principle may be applied to a left foot. That is, user-specific gait information may be obtained by measuring an angle $\beta'2$ formed by the surface of the earth and the ball of the left foot and an angle $\beta2$ formed by the surface of the earth and the kick heel of the left foot.

Although not shown, a signal related to gait information may be obtained by measuring the walking frequency of a user. The action sensing units 111" attached to the feet of a user may send vibration frequencies generated when the user walks to the sensing unit 110". The sensing unit 110" may receive the vibration frequencies so that they are stored in the gait information storage unit 130".

Any one of the stride, and toe-out angle, foot angle, and walking frequency upon walking may be selected and used as gait information about a user. In order to increase accuracy for user-specific information, however, two or more of the stride, and toe-out angle, foot angle, and walking frequency upon walking may be selected and used as gait information.

Tables 1 and 2 below list the above-described characteristics. Table 1 shows gait information about a user 1, and Table 2 shows gait information about a user 2.

TABLE 1

|  | Stride (cm) | Toe-out angle (rad) | Elbow angle (rad) | Heel angle (rad) | Vibration frequency (Hz) |
|---|---|---|---|---|---|
| Right foot | R1: 24.5 | R2: 0.027 π | R3: 0.038 π | R4: 0.044 π | R5: 250 Hz |
| Left foot | L1: 24.2 | L2: 0.031 π | L3: 0.040 π | L4: 0.045 π | L5: 245 Hz |
| Walking frequency |  |  | H1: 1.5 Hz |  |  |

TABLE 2

|  | Stride (cm) | Toe-out angle (rad) | Elbow angle (rad) | Heel angle (rad) | Vibration frequency (Hz) |
|---|---|---|---|---|---|
| Right foot | R1: 24.5 | R2: 0.030 π | R3: 0.034 π | R4: 0.037 π | R5: 230 Hz |
| Left foot | L1: 24.4 | L2: 0.032 π | L3: 0.036 π | L4: 0.040 π | L5: 232 Hz |
| Walking frequency |  |  | H1: 1.4 Hz |  |  |

In Tables 1 and 2, in the case of the stride, the feature symbol R1 may be assigned to the right foot and the feature symbol L1 may be assigned to the left foot. In the case of the toe-out angle, the feature symbol R2 may be assigned to the right foot and the feature symbol L2 may be assigned to the left foot. Furthermore, in the case of the elbow angle, the feature symbol R3 may be assigned to the right foot and the feature symbol L3 may be assigned to the left foot. In the case of the heel angle, the feature symbol R4 may be assigned to the right foot and the feature symbol L4 may be assigned to the left foot. In the case of the vibration frequency, the feature symbol R5 may be assigned to the right foot and the feature symbol L5 may be assigned to the left foot. Furthermore, H1 may be assigned to the walking frequency.

Each of the feature symbols R1 . . . R5, L1 . . . L5, and H1 is raw data collected to digitize gait information, and some or all of the raw data of each feature symbol may be defined as one piece of gait information. Gait information defined as described above is repeatedly collected so that it is matched with a user-specific gait, and an average value of raw data derived accordingly is used, thereby increasing reliability of the gait information. Furthermore, after a specific time, the average value of the raw data is updated to further improve reliability of the gait information. When the sensing unit 110" collects data from the action sensing unit 111", the data may be converted into a digital signal and stored in the information storage unit 130".

Furthermore, the conversion unit 120" according to an embodiment of the present invention may pattern and informatize the digital signal. A method for patterning and informatizing the digital signal may include partitioning a region by setting a boundary for each datum of a specific range and dataficating (or digitizing) the region.

For example, assuming that a pattern 24.*a* is a pattern P1 ranging from 24.0 cm to 24.2 cm and a pattern 24.*b* is a pattern P2 ranging from 24.3 cm to 24.5 cm, it is assumed that a unique pattern of the stride R1 of the right foot of a user 1 is formed in P2, a unique pattern of the stride L1 of the left foot of the user 1 is formed in P1, and thus the unique pattern value of stride-related gait information is represented as (P2, P1). In this case, if the stride of the right foot of the user 1 is measured to be 24.4 cm and the stride of the left foot of the user 1 is measured to be 24.3 cm, the pattern value of current stride-related gait information according to the measured values is (P2, P2), which is different from the unique pattern value (P2, P1) of the stride-related gait information.

It is assumed that a unique pattern of the stride R1 of the right foot of a user 2 is formed in P2, a unique pattern of the stride L1 of the left foot of the user 2 is formed in P1, and thus the unique pattern value of stride-related gait information is represented as (P2, P2). In this case, if the stride of the right foot of the user 2 is measured to be 24.4 cm and the stride of the left foot of the user 2 is measured to be 24.3 cm, the pattern value of current stride-related gait information according to the measured values is (P2, P2), which is the same as the unique pattern value (P2, P2) of the stride-related gait information.

The central management server 200" which receives such gait information recognizes that the information received for the user 1 is not suitable for authentication completion because the unique pattern values (P2, P1) and (P2, P2) of the gait information about the user 1 and the user 2 have already been stored in the user information storage unit 220". Accordingly, the central management server 200" returns a result of an authentication failure to the smart device 100".

Furthermore, the central management server 200" recognizes that the information received for the user 2 is suitable for authentication completion and thus returns a result of an authentication success to the smart device 100".

The gait information to which R2 . . . R5, L2 . . . L5, and H1 have been assigned may also be patterned using the same method as the pattern process, and may be used as gait information suitable for user authentication.

Furthermore, the apparatus for providing a user authentication service according to an embodiment of the present invention may select any one of the stride, and toe-out angle, foot angle, and walking frequency upon walking of the user, may represent the selected information as gait information about the user, and may perform user authentication using the gait information, but may perform user authentication using gait information in association with or in parallel with a bio recognition method, a fingerprint, the iris, a face, and voice recognition, that is, conventional techniques, in order to enhance security.

It is however to be noted that such an example is only one example for obtaining and using gait information according to an embodiment of the present invention and the present invention is not necessarily limited thereto.

In accordance with an embodiment of the present invention, the apparatus for providing a user authentication service may further include a correction unit (not shown) configured to correct gait information sensed with respect to a variable value according to the geographic features of a footpath. A user may walk on an uneven road surface, an incline plane or a curved runway in addition to a flatland. In this case, the correction unit may be used to correct an error rate of gait information obtained through the sensing unit 110", which may suddenly increase when compared with unique information included in previously stored user information. As an example of a correction method, the correction unit may perform + and/or − correction on data, corresponding to real-time gait information, based on the GPS data of geographic features.

A method for providing a user authentication service using a gait according to an embodiment of the present invention is described below with reference to FIGS. 25 and 26.

Figure 25:
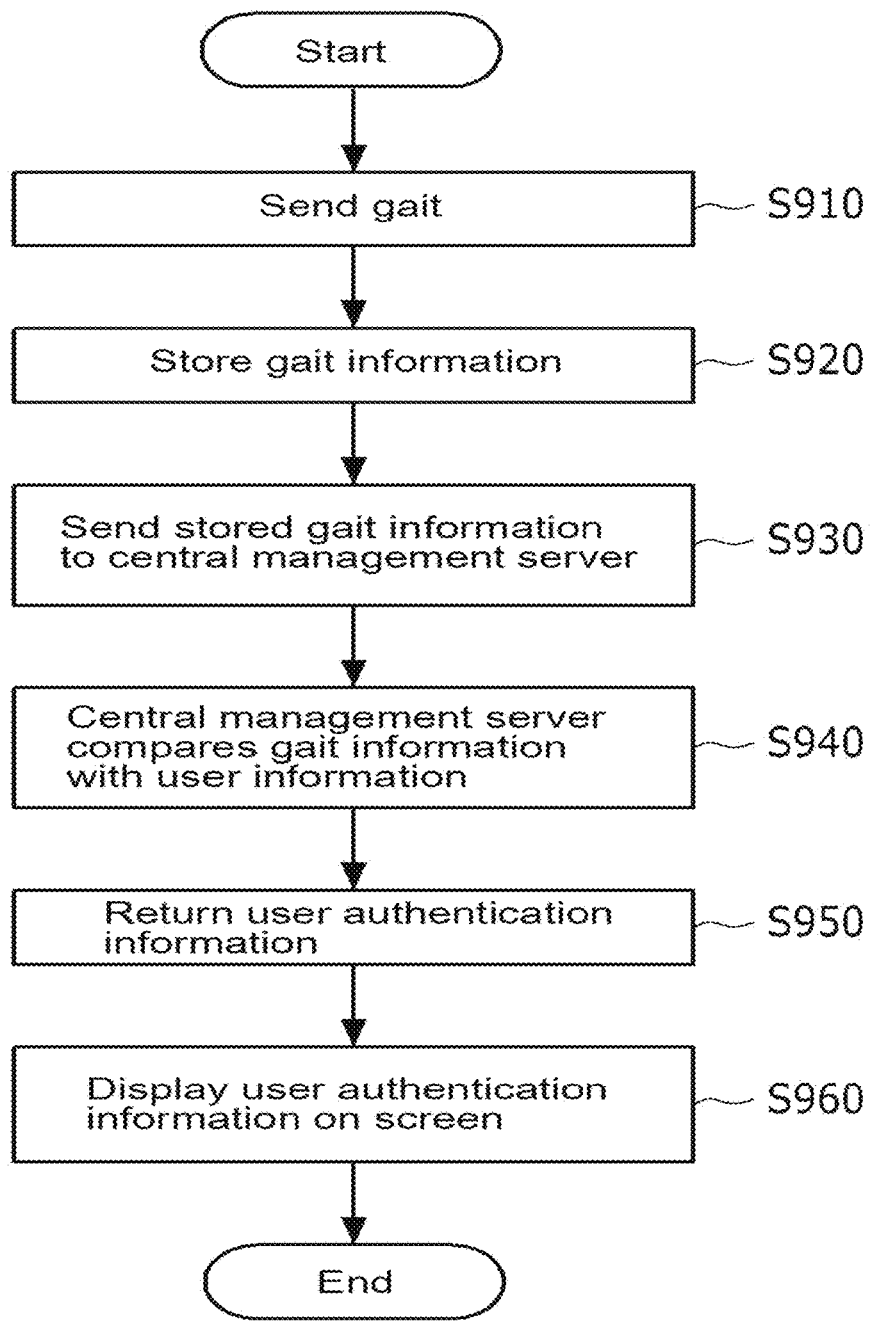
FIG. 25 is a flowchart illustrating a method for providing a user authentication service using a gait according to an embodiment of the present invention.

FIG. 25 is a flowchart illustrating a method for providing a user authentication service using a gait according to an embodiment of the present invention.

Figure 26:
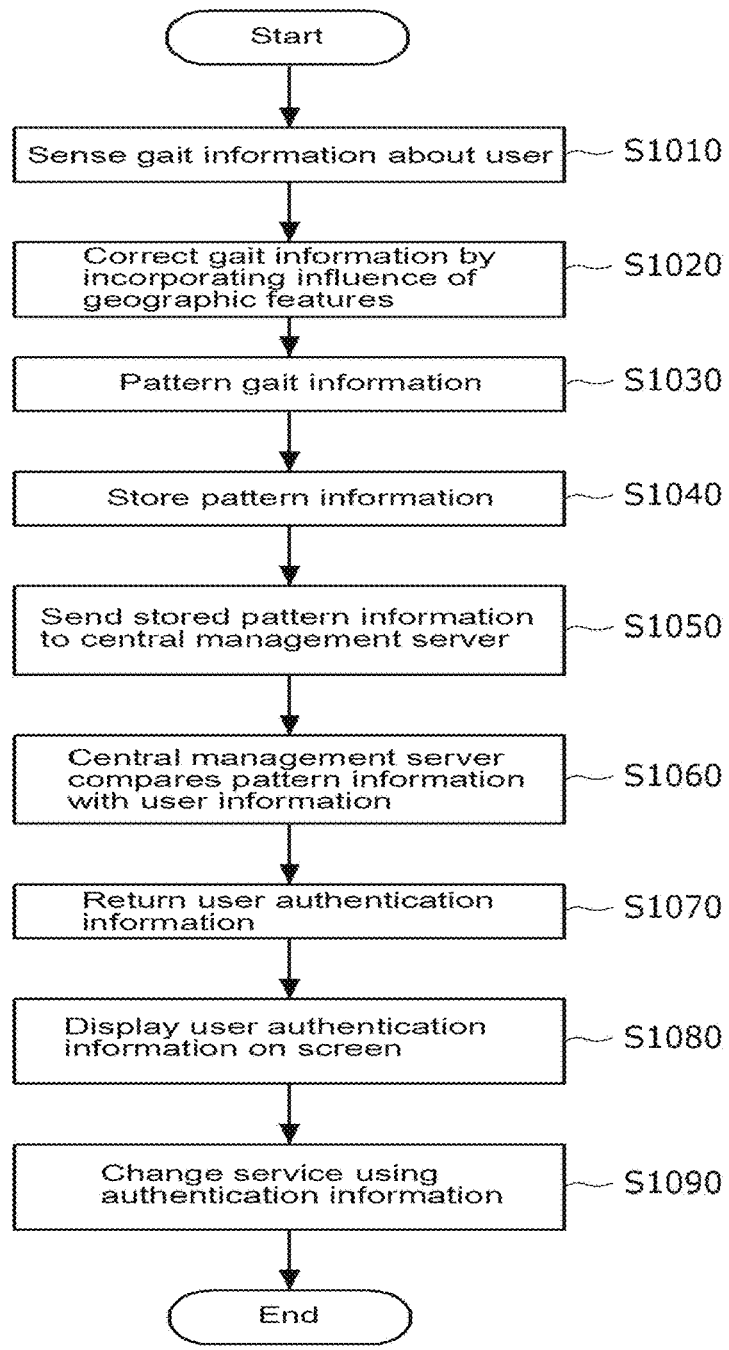
FIG. 26 is a flowchart illustrating a method for providing a user authentication service using a gait according to another embodiment of the present invention.

FIG. 26 is a flowchart illustrating a method for providing a user authentication service using a gait according to another embodiment of the present invention.

The method according to an embodiment of the present invention is a method for providing a user authentication service based on the smart device, and may include step S910 for sensing the gait of a user, step S920 for storing the sensed gait information, step S930 for transferring the gait information to the central management server using the data transmission unit, step S940 for receiving user authentication information through the data reception unit from the central management server, and step S950 for displaying the user authentication information, received by the data reception unit, on a screen.

At step S910, as described above, the gait information of the user may be obtained using the sensing unit 110" or using the sensing unit 110" and the action sensing unit 111" provided independently of the sensing unit 110". In this case, when the obtained gait information is accumulated, it may be defined as user-specific gait information and stored in the user information storage unit 220" of the central management server 200". The stored user-specific gait information may be extracted and used when user authentication is performed.

At step S920, the gait information obtained through the sensing unit 110" is stored temporally or permanently. In this case, the above-described real-time gait information and/or unique information may correspond to the stored gait information. Related data that belongs to the obtained gait information and that includes noise may be filtered at step S920.

At step S930 according to an embodiment of the present invention, the data transmission unit 130" sends the gait information to the central management server 200" using wired/wireless communication.

In accordance with an embodiment of the present invention, the method may include step (not shown) for comparing the received gait information with previously stored user information. Step (s940) for comparing the gait information with the previously stored user information may be performed in the central management server 200". In this case, the previously stored user information may correspond to gait unique information previously registered by the user.

Furthermore, step S950 for receiving user authentication information from the central management server through the data reception unit may include returning the user authentication information. Such a process may be performed in such a manner that the central management server 200" sends the user authentication information to the smart device 100" as a result of the comparison and the user authentication information is received through the data reception unit 150" of the smart device 100".

At step S960, the user authentication information is displayed on a screen. Accordingly, information regarding whether login or security authentication has succeed or failed is provided to the user.

A method for providing a user authentication service using a gait according to another embodiment of the present invention is performed as follows.

Referring to FIG. 26, the method for providing a user authentication service using a gait according to another embodiment of the present invention may include step S1010 for sensing the gait of a user, step S1020 for correcting the gait by incorporating the influence of geographic features into the gait, step S1030 for patterning (or digitizing) the gait, step S1040 for storing the pattern information, step S1050 for sending the pattern information to the central management server using the data transmission unit, step S1060 for comparing the pattern information received from the central management server 200" with previously stored user information, step S1070 for returning user authentication information as a result of the comparison, step S1080 for displaying the user authentication information received through the data reception unit, and step S1090 for changing an existing service into a service using the authentication information.

Unlike in the embodiment of FIG. 25, in the embodiment of FIG. 26, correction may be performed by incorporating the influence of geographic features into the gait of the user, and the gait information may be patterned (or digitized). Furthermore, service data may be changed using the user authentication information. The step for correcting the gait by incorporating the influence of geographic features into the gait and the step for patterning the gait information have been described in detail above, and a detailed description thereof is omitted.

The step for changing an existing service into a service using the authentication information refers to switching to a user-customized service after user authentication is completed.

More specifically, the user-customized service refers to a service in which gait information is sensed again when user authentication fails or a user subscription request site is connected if user authentication has failed in plural times and refers to a service in which the right to access an available service is assigned to only a user who has been registered with the user information storage unit 220".

As one of the major characteristics of the present invention, if gait information received while a user who holds the smart device 100" including the sensing unit 110", the storage unit 130", the data transmission unit 140", and data reception unit 150", and the display unit 160" according to an embodiment of the present invention walks is matched with user information registered with the central management server 200", user authentication can be performed and an existing service can switch to a user-customized service although the smart device 100" held by the user is one owned by another user.

Furthermore, in accordance with an embodiment of the present invention, the gait of a user may be sensed in real time, the sensed gait information may be compared with information about the user for a set time even after user authentication is completed, and updated user authentication information may be received as a result of the comparison.

If user authentication has failed, it may succeed when gait information is compared with the user information again. Although user authentication has succeeded, if gait information is not identical with user information for a set time as a result of a comparison, the comparison unit 240" of the central management server 200" may determine the user authentication to have failed.

As described above, in accordance with an embodiment of the present invention, gait information about the gait of a user is collected using the smart device, and a user authentication service is provided using the collected gait information. Accordingly, user authentication of a new paradigm can be performed which is different from conventional bio-based user authentication methods, such as fingerprint recognition, face recognition, iris recognition, and vein recognition.

Furthermore, a benefit, such as digital content (or a coupon) conforming with the smart era, can be provided to a user whose authentication has succeeded because a service associated with digital content is provided in real time in relation to user authentication.

Furthermore, in accordance with an embodiment of the present invention, although the smart device held by a user is one owned by another person, user authentication can be performed. If user authentication is completed, a method for switching to a user-customized service is also provided.

The method for providing a user authentication service using a gait may be written in a program form, and pieces of code and code segments that form the program may be easily reasoned by a programmer skilled in the art. Furthermore, a program regarding the method for providing a user authentication service using a gait may be stored in information storage media readable by an electronic device and may be read and executed by an electronic device.

Furthermore, the method according to an embodiment of the present invention may be implemented in the form of a program or application for executing the method. A computer-readable recording medium on which such a program or application has been recorded should be included in the scope of the present invention.

As described above, those skilled in the art to which the present invention pertains will appreciate that the present invention may be implemented in other detailed forms without changing the technical spirit or essential characteristic of the present invention. Accordingly, it is to be understood that the aforementioned embodiments are only illustrative and do not have a limited range. It is also to be noted that the illustrated flowchart is merely sequential order illustrated to achieve the most preferred results in implementing the present invention, and other additional steps may be provided or some of the steps may be deleted.

Technological characteristics described in this specification and an implementation for executing the technological characteristics may be implemented using a digital electronic circuit, may be implemented using computer software, firmware or hardware including the structure described in this specification and structural equivalents thereof, or may be implemented using a combination of one or more of them. Furthermore, the implementation for executing the technological characteristics described in this specification may be implemented in the form of a computer program product, that is, a module regarding computer program instructions encoded on a kind of program storage media in order to control the operation of a processing system or for execution by the processing system.

A computer-readable medium may be a machine-readable storage device, a machine-readable storage substrate, a memory device, a composition of materials that affect a machine-readable electromagnetic signal or a combination of one or more of them.

In this specification, the term "apparatus (or device)" or "system" covers all apparatuses, devices, and machines for processing data, for example, including a processor, a computer or a multi-processor, or a computer. The processing system may include, for example, code that forms processor firmware, a protocol stack, a database management system, an operating system, or all types of code that form an execution environment for a computer program when a combination of one or more of them is requested, in addition to hardware.

A computer program also known as a program, software, a software application, a script or code may be written in any form of a programming language which includes a compiled or interpreted language or a transcendental and/or procedural language, and may also be implemented in any form including an independent program or module, a component, a subroutine or other units suitable for being used in a computer environment.

The computer program does not need to necessarily correspond to a file of a file system. The program may be stored in a single file provided to a requested program, multiple files that interact with each other (e.g., a file that stores one or more modules, a lower program or part of code), or another program or part of a file including data (e.g., one or more scripts stored in markup language document).

The computer program may be located in a single site or distributed to a plurality of sites and may be implemented to be executed on multiple computers or one or more computers interconnected over wired/wireless communication networks.

A computer-readable medium suitable for storing computer program instructions and data may include semiconductor memory devices, such as EPROM, EEPROM, and a flash memory device, for example, all types of non-volatile memory, media, and memory devices including magnetic disks, such as an internal hard disk or an external disk, magneto optical disks, CDs, and DVDs. The processor and the memory may be supplemented by a logic circuit for a special object or may be integrated into the logic circuit for a special object.

An implementation for executing the subject matter described in this specification may be implemented in an operation system including a backend component, such as a data server, a middleware component, such as an application server, a frontend component, such as a client computer having a web browser or graphic user interface capable of interacting with the implementation of the subject matter described by a user in this specification or all combinations of one or more of the backend, middleware, and frontend components. The component of the system may be accessed by any type or medium for digital data communication, such as a communication network.

Hereinafter, more detailed embodiments capable of implementing the above-described contents and the system and the method described in this specification described in this specification are described in detail.

The system and method described in this specification may be used partially or generally through a server related to a client device or web-based storage system or means for executing computer software, program code or instructions on one or more processors included in a server. In this case, the processor may be part of a server, a client, network infrastructure, or a computing platform, such as a mobile computing platform or fixed computing platform. More specifically, the processor may be a kind of computer or processing device capable of executing program instructions, code, etc. Furthermore, the processor may further include memory for storing the method, instructions, code or program. If memory is not included in the processor, the processor may access a storage device, such as CD-ROM, DVD, memory, a hard disk, a flash drive, RAM, ROM, or a cache in which the method, instructions, code or program.

Furthermore, the system and method described in this specification may be used partially or generally through an apparatus for executing computer software on a server, a client, a gateway, a hub, a router or network hardware. In this case, the software may be executed in various types of servers, such as a file server, a print server, a domain server, an Internet server, an intranet server, a host server, and a distributed server. The aforementioned servers may further include memory, a processor, a computer-readable storage medium, a storage medium, a communication device, a port, a client, and an interface capable of accessing other servers over wired/wireless networks.

Furthermore, the method, instructions or code may also be executed by a server. Other devices required to execute the method may be implemented as part of a hierarchical structure associated with the server.

Furthermore, the server may provide an interface to other devices including a client, another server, a printer, a database server, a print server, a file server, communication a server, and a distributed server without limitation. A connection through the interface may enable a program to be easily executed at a remote place over wired/wireless networks.

Furthermore, any one of devices connected to the server through the interface may further include at least one storage device capable of storing the method, instructions or code. The central processor of the server may provide instructions, code, etc. to be executed on another device to the device so that the instructions, code, etc. are stored in a storage device.

The system and the method described in this specification may be used partially or generally through network infrastructure. In this case, the network infrastructure may include all of devices, such as a computing device, a server, a router, a hub, a firewall, a client, a personal computer, a communication device, and a routing device, and separate modules capable of executing respective functions. The network infrastructure may further include storage media, such as story flash memory, a buffer, a stack, RAM, and ROM, in addition to the aforementioned devices and module. Furthermore, the method, instructions or code may also be executed by and stored in any one of the device, module, and storage medium included in the network infrastructure. Another device required to execute the method may also be implemented as part of the network infrastructure.

Furthermore, the system and method described in this specification may be implemented using hardware or hardware suitable for a specific application and software. In this case, the hardware includes all of general-purpose computer devices, such as a personal computer and a mobile communication terminal, and a business type specific computer device. The computer device may be implemented using a device, such as memory, a microprocessor, a microcontroller, a digital signal processor, an application-specific integrated circuit, a programmable gate array, programmable array logic or a combination of them.

The aforementioned computer software, instructions, code, etc. may be stored or accessed by a readable device. In this case, the readable device may include memory, such as a computer component including digital data used for computing for a specific time, semiconductor storage, such as RAM or ROM, permanent storage, such as an optical disk, high-capacity storage, such as a hard disk, a tape and a drum, optical storage, such as a CD or DVD, and network access type storage, such as flash memory, a floppy disk, a magnetic tape, a paper tape, an independent type RAM disk, high-capacity storage detachable from a computer, dynamic memory, static memory, variable storage, and cloud. In this case, the instructions, code, etc. include all of languages, such as data-oriented languages, such as SQL and dBase, system languages, such as C, Objective C, C++, and Assembly, architecture languages, such as Java and NET, and application languages, such as PHP, Ruby, Perl, and Python, but are not limited thereto. The instructions, code, etc. may include all of languages widely known to those skilled in the art to which the present invention pertain.

Furthermore, the "computer-readable medium" described in this specification includes all of media which contribute to the provision of instruction to a processor in order to execute a program. More specifically, the "computer-readable medium" includes non-volatile media, such as a data storage device, an optical disk and a magnetic disk, volatile media, such as dynamic memory, and transmission media, such as a coaxial cable, a copper wire and an optical fiber for sending data, but is not limited thereto.

The elements for executing the technical characteristics of the present invention included in the block diagrams and flowcharts shown in the accompanying drawings of this specification mean the logical boundary between the elements.

In accordance with a software or hardware embodiment, however, the functions of the illustrated elements and functions thereof may be implemented so that the elements and functions thereof are executed in the form of an independent software module, a monolithic software structure, code, a service or a combination of them and are stored in a medium which is executable by a computer including a processor capable of executing stored program code and instructions. Accordingly, all of such embodiments should be construed as belonging to the scope of the present invention.

Accordingly, the accompanying drawings and technologies thereof describe the technical characteristics of the present invention, but should not be simply reasoned unless a specific array of software for implementing such technical characteristics is clearly described otherwise. That is, the aforementioned various embodiments may be present and may be partially modified while having the same technical characteristics as those of the present invention. Accordingly, such modified embodiments should be construed as belonging to the scope of the present invention.

Furthermore, the flowchart describes operations in the drawing in a specific sequence, but has been illustrated to obtain the most preferred results. It should not be understood that such operations must be executed or all the illustrated operations must be executed in the illustrated specific sequence or sequential order. In a specific case, multitasking and parallel processing may be advantageous. Furthermore, the separation of various system components in the aforementioned embodiments should not be construed as requesting such separation in all the embodiments. It should be understood that the aforementioned program components and systems may be integrated into a single software product or packaged into a multi-software product.

In accordance with an embodiment of the present invention, an accurate quantity of motion of a user can be measured by analyzing the quantity of motion with consideration taken of information about the body of the user, such as the age, sex, height, weight, and body composition of the user, along with a movement of the user in measuring the quantity of motion of the user.

Furthermore, an embodiment of the present invention can provide pieces of information about fitness equipment, sporting goods, food, and a coupon so that a user can keep a desired amount of muscle, body fat, etc. based on information about the body composition, the quantity of motion, etc. of the user.

Furthermore, in accordance with an embodiment of the present invention, a user can frequently perform self-analysis conveniently regardless of age or sex without a burden because he or she can measure his or her body composition through a vein authentication procedure.

Furthermore, an embodiment of the present invention can prevent private use of public payment means because payment is not performed even through a user has sharing payment means, but can be performed only when an activation condition in which the sharing payment means is used is satisfied.

In accordance with an embodiment of the present invention, user authentication of a new paradigm can be performed because gait information about the gait of a user is collected using the smart device and a user authentication service is provided using the collected gait information.

Furthermore, a benefit, such as digital content (e.g., a coupon) conforming with the smart era, can be provided to a user whose authentication has succeeded because a service associated with digital content is provided to the user in real time in relation to user authentication.

Furthermore, in accordance with an embodiment of the present invention, although the smart device held by a user is one owned by another person, user authentication can be performed. If user authentication is completed, a method for switching to a user-customized service is also provided.

Furthermore, a payment service can be safely provided to a user although the user has lost his or her wearable device because the user is authenticated using authentication information when the user performs payment using sharing payment means.

Furthermore, an embodiment of the present invention can help a user to keep a balanced body because the amount of action of each part of the body of the user is checked, the amounts of muscle and body fat of parts of the body are compared, and the user is notified of an imbalanced body part.

As described above, this specification is not intended to limit the embodiments of the present invention by the proposed detailed terms. Accordingly, although the present invention has been described in detail in connection with the aforementioned embodiments, a person having ordinary skill in the art to which the present invention pertains may alter, change, and modify the embodiments without departing from the scope of the present invention.

The scope of the present invention is defined by the appended claims rather than the detailed description, and the present invention should be construed as covering all modifications or variations derived from the meaning and scope of the appended claims and their equivalents.

What is claimed is:

1. A wearable device for vein authentication, comprising:
   a measurement module configured to measure a pattern of veins of a user;
   a communication module configured to send unique bio information about the user measured by the measurement module to a management server along with authentication information and to receive feedback information for the transmitted information from the management server; and
   a memory module configured to store the pattern of the veins of the user,
   wherein the measurement module comprises
   a current measurement device configured to measure the pattern of the veins of the user by passing a fine current through the veins of the user, and
   a current transmission device configured to measure a body composition of the user by passing a current through cells within the body of the user,
   wherein the feedback information provides at least one of fitness equipment information, sporting goods information, food information, and a coupon information corresponding to the body composition of the user.

2. The wearable device of claim 1, wherein the measurement module notifies the user whether the pattern of the veins measured by the measurement module is identical with a previously stored pattern of the veins of the user using the pattern of the veins measured by the measurement module.

3. The wearable device of claim 1, wherein the measurement module measures an amount of muscle or body fat of each part of the body of the user and notifies the user of an imbalanced body part.

4. A method for providing feedback information through vein authentication, comprising:
   a vein information acquisition step for obtaining, by a wearable device, vein information using a current measurement device by passing a fine current through veins of a user;
   a vein authentication step for identifying a user by comparing the vein information obtained at the vein information acquisition step with existing vein information;
   a communication step for sending unique bio information about the user obtained at the vein information acquisition step to a management server along with authentication information and receiving feedback information for the transmitted information from the management server;
   a storage step for storing contents at the vein information acquisition step, the vein authentication step, and the communication step in the wearable device, and
   a service providing step for providing, by the wearable device, feedback information,
   wherein the service providing step comprises steps of:
   (a) measuring a body composition or movement of the user by passing a current through cells within the body;
   (b) calculating a change of the body composition or movement of the user; and
   (c) sending, by a communication module, information about the measured body composition or measured quantity of motion to the management server and receiving the feedback information for the transmitted information from the management server, wherein the feedback information includes at least one of fitness equipment information, sporting goods information, food information, and coupon information corresponding to body information about a body of the user based on results of a measurement of the vein information of the user.

5. The method of claim 4, wherein the vein authentication step comprises:
   an initial input step for setting a pattern of the veins of the user;
   a vein pattern reception step for receiving a pattern of the veins obtained in real time when the user uses the wearable device; and
   an authentication step for identifying the user by comparing the pattern of the veins inputted at the initial input step with the pattern of the veins obtained in real time.

6. The method of claim 4, wherein the communication step comprises steps of:
   (a) receiving the vein information obtained at the vein information acquisition step;
   (b) receiving the authentication information obtained through the identification of the user and the comparison at the vein authentication step; and
   (c) sending, by a communication module, the obtained vein information and authentication information to the management server and receiving the feedback information for the transmitted information from the management server.

7. The method of claim 4, wherein the communication step comprises:
   (a) storing, by a database of the management server, user information or the feedback information;
   (b) receiving, by a communication unit of the management server, the obtained vein information and authentication information of the user from the wearable device;
   (c) selecting, by a server control unit of the management server, feedback information from a database based on the received vein information and authentication information; and
   (d) sending, by a server communication unit of the management server, the information selected by the server control unit to the wearable device.

* * * * *